(12) United States Patent
Nath

(10) Patent No.: US 8,057,429 B2
(45) Date of Patent: Nov. 15, 2011

(54) FEEDING TUBE

(76) Inventor: Iyunni Venkata Sesha Sayi Nath, Seminole, FL (US)

(*) Notice: Subject to any disclaimer, the term of this patent is extended or adjusted under 35 U.S.C. 154(b) by 101 days.

(21) Appl. No.: 12/393,717

(22) Filed: Feb. 26, 2009

(65) Prior Publication Data
US 2009/0216186 A1    Aug. 27, 2009

Related U.S. Application Data

(60) Provisional application No. 61/031,442, filed on Feb. 26, 2008, provisional application No. 61/113,697, filed on Nov. 12, 2008.

(51) Int. Cl.
*A61M 29/00*    (2006.01)
(52) U.S. Cl. ................................. 604/97.02
(58) Field of Classification Search ........ 604/96.01, 604/97.02, 101.01, 103.05, 104, 513, 514, 604/910; 606/108, 192
See application file for complete search history.

(56) References Cited

U.S. PATENT DOCUMENTS

| | | |
|---|---|---|
| 4,393,873 A | 7/1983 | Nawash et al. |
| 4,834,725 A | 5/1989 | Iwatschenko |
| 5,073,166 A | 12/1991 | Parks et al. |
| 5,074,846 A | 12/1991 | Clegg et al. |
| 5,112,310 A | 5/1992 | Grobe |
| 5,151,086 A | 9/1992 | Duh et al. |
| 5,167,627 A | 12/1992 | Clegg et al. |
| 5,342,321 A | 8/1994 | Potter |
| 5,374,252 A | 12/1994 | Banks et al. |
| 5,374,254 A | 12/1994 | Buma |
| 5,391,159 A | 2/1995 | Hirsch et al. |
| 5,454,790 A | 10/1995 | Dubrul |
| 5,458,583 A * | 10/1995 | McNeely et al. ........ 604/103.13 |
| 5,628,753 A | 5/1997 | Cracauer et al. |
| 5,807,314 A | 9/1998 | Ross et al. |
| 5,851,195 A | 12/1998 | Gill |
| 6,004,328 A | 12/1999 | Solar |
| 6,015,400 A | 1/2000 | Ross et al. |
| 6,030,364 A | 2/2000 | Durgin et al. |
| 6,090,073 A | 7/2000 | Gill |

(Continued)

FOREIGN PATENT DOCUMENTS
EP    0497135 B1    12/1995
(Continued)

OTHER PUBLICATIONS http://www.gihealth.com/html/education/printable/printPeg.html, "Percutaneous Endoscopic Gastrostomy (PEG)".

(Continued)

*Primary Examiner* — Christopher D Koharski
(74) *Attorney, Agent, or Firm* — Christopher Paradies; Fowler White Boggs P.A.

(57) ABSTRACT

An feeding tube and a kit for installation of a feeding tube includes a balloon anchored gastric tube. A protective sleeve on a dilator protects the toroidal balloon from damage during surgical insertion of the feeding tube. An integrated gastro jejunal feeding tube unit may include a jejunal tube outlet port at one end, a jejunal balloon port, a gastric sleeve outlet port, one or more gastric balloon ports, one or more gastric balloons, gastric drainage holes, a jejunal balloon positioned at end of the jejunal tube and sleeve. Drainage holes may be provided in the jejunal tube and/or the gastric sleeve. Drainage holes in the gastric sleeve may be used to deflate the stomach, while nutrition is provided by a jejunal tube inserted in the jejunum, simultaneously.

20 Claims, 14 Drawing Sheets

U.S. PATENT DOCUMENTS

| | | |
|---|---|---|
| 6,322,495 B1 | 11/2001 | Snow et al. |
| 6,454,785 B2 | 9/2002 | De Hoyos Garza |
| 6,527,748 B1 | 3/2003 | Suzuki |
| 6,537,247 B2 * | 3/2003 | Shannon .................. 604/103.05 |
| 6,582,395 B1 | 6/2003 | Burkett et al. |
| 6,765,122 B1 | 7/2004 | Stout |
| 6,808,519 B2 * | 10/2004 | Fanelli et al. ................. 604/523 |
| 6,960,199 B2 | 11/2005 | Burkett et al. |
| 7,018,373 B2 | 3/2006 | Suzuki |
| 7,156,860 B2 | 1/2007 | Wallsten |
| 2003/0225393 A1 | 12/2003 | McMichael et al. |
| 2004/0044330 A1 | 3/2004 | Li et al. |
| 2004/0148004 A1 | 7/2004 | Wallsten |
| 2004/0220516 A1 | 11/2004 | Solomon et al. |
| 2005/0165426 A1 | 7/2005 | Manzo |
| 2005/0256455 A1 | 11/2005 | Weststrate et al. |
| 2007/0016172 A1 | 1/2007 | Charukhchian |
| 2007/0088280 A1 | 4/2007 | Gomez |
| 2007/0156117 A1 | 7/2007 | Adams et al. |

FOREIGN PATENT DOCUMENTS

| | | |
|---|---|---|
| EP | 1334744 B1 | 9/2005 |
| WO | WO 01/87226 A2 | 11/2001 |

OTHER PUBLICATIONS http://www.sages.org/sg_asgepub1017.html, "Role of Percutaneous Endoscopic Gastrostomy".

Miller et al., Gastrointestinal Endoscopy. "The Russell percutaneous endoscopic gastrostomy", vol. 34, No. 4, 1988.

Russell et al., American Journal of Surgery. "The Percutaneous Gastrostomy", vol. 184, Jul. 1984.

Boston Scientific Corporation, Brochure for "Resolution (TM) Clip Device", 2006.

C.R. Bard, Inc., Brochsure for "Bard Enteral Feeding Tube Catalog" 2008.

International Search Report dated Aug. 31, 2009, for the corresponding International Application, PCT/US2009/035315, 3 pages.

* cited by examiner

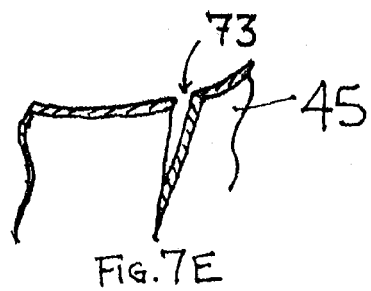
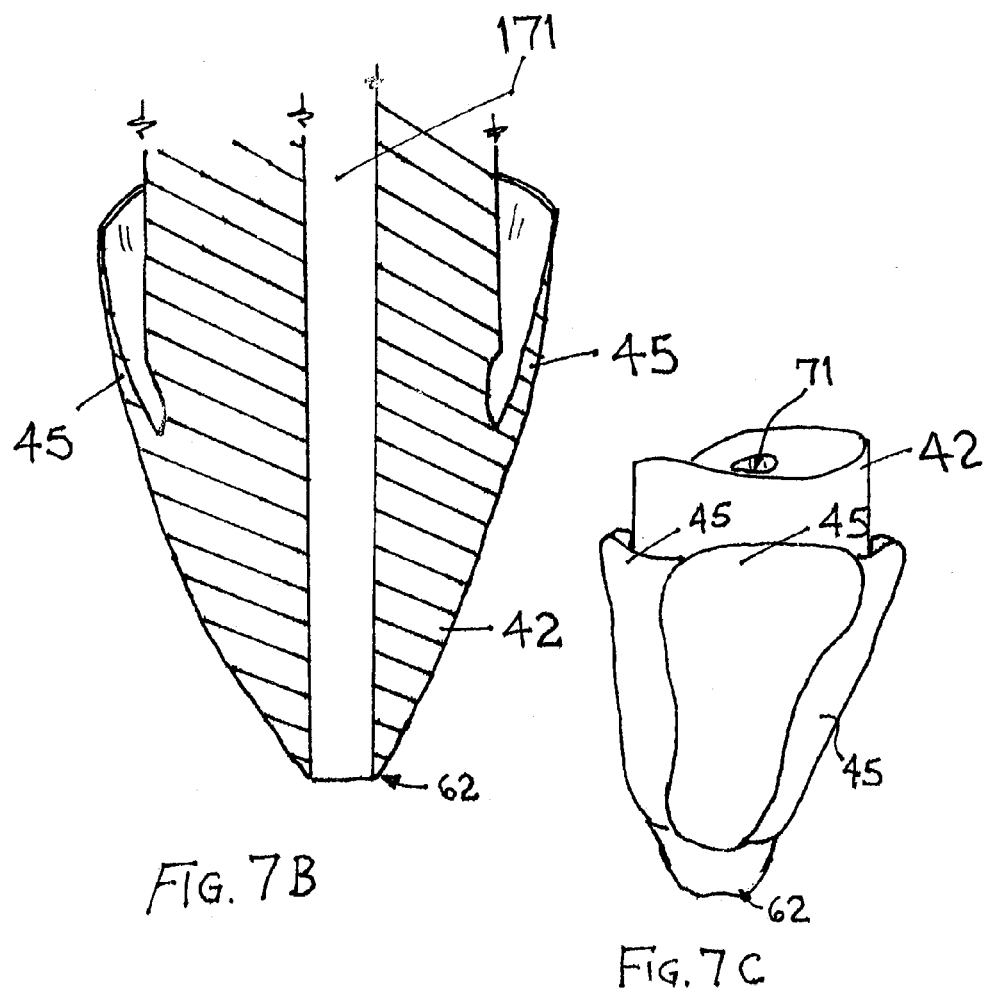

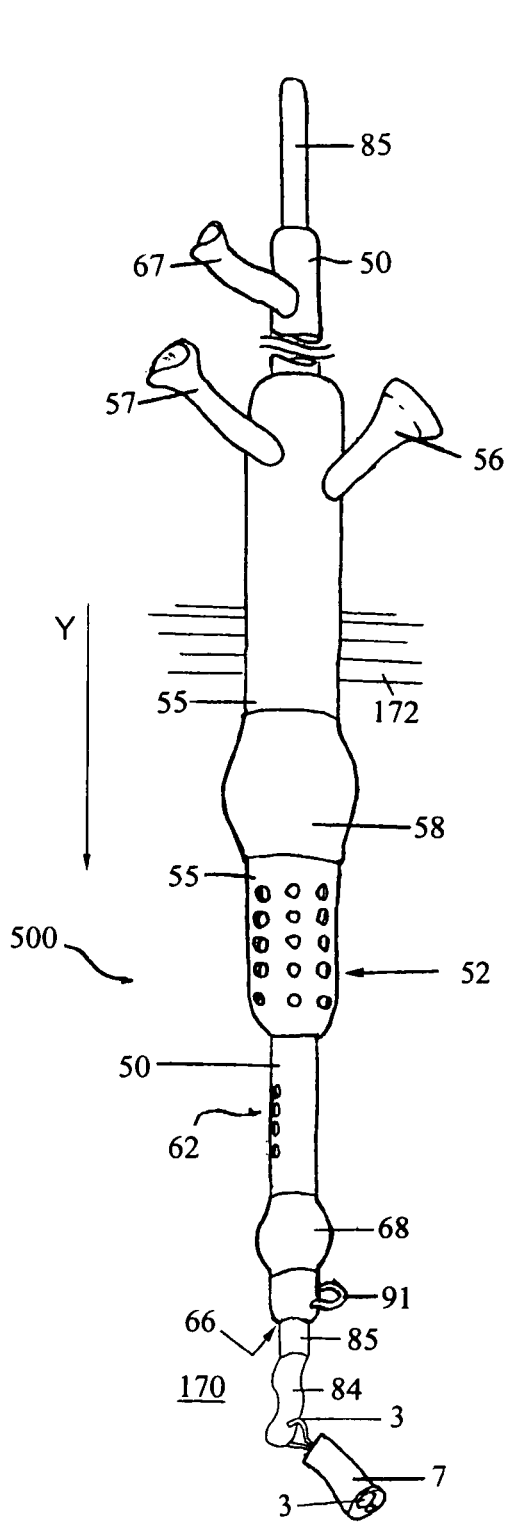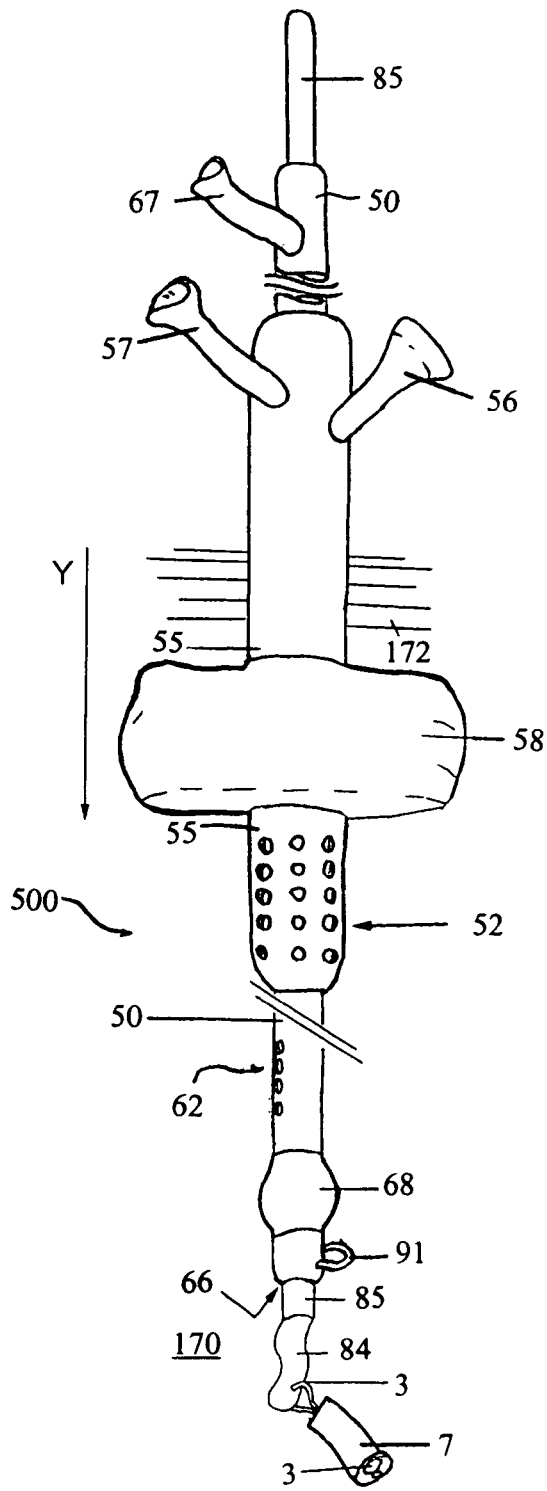
FIG. 9
FIG. 10

FEEDING TUBE

CROSS RELATED APPLICATIONS

The Applicant claims the benefit of and priority to U.S. patent application Ser. No. 61/031,442, filed Feb. 26, 2008, and U.S. patent application Ser. No. 61/113,697, filed Nov. 12, 2008, and the Applicant incorporates by reference herein the entire specification of both of applications.

FIELD OF THE INVENTION

The field relates to total parenteral nutrition, nasogastric tubes, gastrostomy, and related methods in which feeding a patient bypasses mastication and ingestion.

BACKGROUND

Conventional nasogastric tubes have been in use for many years. Complications include trauma related to tube insertion and effects from use of the tube for prolonged periods of time. Occasionally, severe complications such as tracheo-esophageal fistula and perforation of various organs have been reported. Gastrointestinal bleeding of various magnitudes also can occur but less frequently. In addition, feeding tubes inserted through the nose or mouth are acceptable for short period, but such tubes must be replaced by other means for extended delivery of nutrition.

As described in U.S. Pat. No. 6,554,700, patients for which normal ingestion of food becomes difficult or impossible, may require placement of a feeding tube to assist in providing their nutritional needs. For some individuals, such as comatose patients, stroke victims, or those with a compromised gastrointestinal tract, this may require placement of a tube that is introduced percutaneously into the stomach for delivery of nutritional products and medication.

In percutaneous endoscopic gastrostomy (PEG), the procedure involves introduction of a gastroscope into the stomach, while the desired site where a stoma is to be created, occurs by depressing the abdomen. A sheathed needle punctures the abdominal wall and enters the stomach, creating a stoma. The needle is removed and a looped insertion wire is introduced through the sheath where it is grasped by a snare deployed from a working channel of the gastroscope. Once it is captured, the insertion wire is pulled into the channel of the gastroscope. The gastroscope is then withdrawn from the patient via the oral cavity, pulling the wire with it.

In the standard Ponsky method (or "pull" method), the distal loop of a percutaneous gastrostomy feeding tube is coupled to the insertion wire loop exiting the patient's mouth. With the insertion wire now tethered to the gastrostomy feeding tube, the endoscopist then retracts the insertion wire exiting the stoma, thereby pulling the gastrostomy feeding tube into the patient's mouth and on toward the stomach. The tapered dilator portion aids in allowing the gastrostomy feeding tube to pass through the stoma. Once the tube has been properly positioned with the end cap snug against the internal wall of the stomach, the dilator portion of the gastrostomy feeding tube is cut away. Finally, the internal position of the gastrostomy feeding tube is checked by reintroducing the gastroscope.

As described in U.S. Pat. No. 5,073,166, the pull procedure has several disadvantages, one of which is the fact that, for both emplacement and removal, an endoscope must be inserted into the patient's esophagus, requiring anesthesia and causing discomfort to the patient. Also, the catheter itself must pass through the patient's esophagus, once for emplacement and once for removal. This becomes even more problematic when secondary or replacement catheters are put in place, since each time the catheter is changed, the "pull" procedure must again be followed, with increased likelihood of trauma, infections, and other complications.

Furthermore, the pull procedure is particularly difficult to carry out when a patient has an obstruction in the esophagus, which is a problem compounded by the fact that it is just such people who are likely to need the procedure. When there is an obstructive lesion in the esophagus, one may need to dilate the narrowed area to perform the procedure. This may expose the patient to a higher risk of bleeding or perforation as the tethered tube is pulled blindly during the procedure. Another disadvantage arises from the fact that infectious or cancerous matter may be drawn from a diseased area in, for example, the throat, down into the stomach, with the possibility of spreading the disease further, especially to the area around the freshly formed opening in the stomach.

In the variation of a percutaneous endoscopic gastrostomy procedure known as the "push" method or the Russell procedure, the gastrostomy feeding tube is a pull wire, but is pushed down the esophagus by the physician and into positioned in the stomach. As with the "pull" method, the gastroscope is usually reintroduced to verify that the end cap is properly positioned against the stomach wall. In the Russell procedure, a needle is first inserted into the stomach (at a site located by endoscopy, as with the pull procedure), and then a guide wire is inserted through a lumen in the needle. A small incision is then made in the fascia next to the guide wire, after which an interiorly lubricated sheath having a splittable seam is guided, along with a tapered dilator, over the guide wire and into the stomach. Once the sheath is in place, the dilator and guide wire are removed, and a balloon catheter is inserted through the lubricated central lumen of the sheath. A distal balloon of the catheter is then inflated, and the sheath is peeled or split away along its seam or seams, thus leaving the catheter emplaced in the stomach. Sutures are provided to maintain tension of the balloon against the peritoneum. However, the splittable sheath is necessarily larger in diameter than the catheter which is inserted through it for emplacement within the stomach. Therefore, the opening into the stomach is made overly large, making sealing difficult and increasing the likelihood of infection. The sheath may not be made too narrow, or the physician will not be able to insert the catheter through it, and thus there is a trade-off between insertability of the catheter and the quality of the seal once the catheter is in place; the dilator must closely follow the line of the guidewire, so as not to buckle the wire into the peritoneal cavity. Occasionally, during placement of the feeding tube, the dilator is removed and the peelable sheath is left behind in the stomach, allowing air in the distended stomach to escape, causing the stomach to collapse. Then a patient must be taken to the operation theater for an open placement feeding tube insertion.

A procedure known as Sacks-Vine involves passing an endoscope down the throat until its terminus is in the interior of the stomach. A Seldinger needle is then externally inserted through the various tissue layers until it enters the stomach at a predetermined point. The needle is retracted leaving only the Seldinger cannula in place and a guidewire is then inserted through the stoma. The terminal end of the guidewire is grabbed by the endoscope and retracted up the throat. A tapered dilating catheter attached to the gastrostomy port is passed over the guidewire then inserted down the throat, through the esophagus and into the stomach so as to form, upon removal of the catheter through the abdominal skin, an opening wide enough to accommodate a trailing gastric port.

At the proximal end of the gastrostomy port is a retention device that keeps the proximal end of the catheter from passing through the gastrocutaneous stoma. A feeding set adapter is then hooked up to the portion of the catheter external of the body that allows the gastrostomy port to be used for the actual feeding of the patient. Like the pull method, the Sacks-Vine procedure requires another endoscopic procedure for removal of the tube upon cessation of enteral feeding or upon the necessity of changing the tube. This additional procedure results in additional trauma associated with any endoscopic procedure, as well as cost, to the patient. In addition, if blind placement of the G tube (i.e., without endoscopic visualization) occurs, re-endoscopy is necessary to exclude trauma in the path of the Q-tube. The procedure may cause trauma and bleeding as the G tube is pushed or pulled. Also, the insertion of the G-tube can be more traumatic if the esophagus has been dilated due to esophageal stricture. If there is a malignant stricture present, there is a risk that the peritoneal space may be seeded with cancerous matter. This procedure is subject to infections from the inside out displacement of the feeding tube.

In yet another technique of feeding described in U.S. Pat. No. 6,322,495, an introducer technique is used. The introducer technique differs from the push and pull techniques in that the feeding tube is inserted through the abdominal wall and not through the mouth. After an endoscope is advanced into the stomach, a T-fastener is placed to move the stomach close to the abdominal wall. A needle is inserted through the abdominal wall into the stomach to create an opening. A guide wire is advanced through the opening, and an introducer with a peel-away sheath is passed over the guide wire. The introducer is then removed, and a gastrostomy tube is inserted into the stomach through the peel-away sheath. The feeding tube is a catheter with a Foley balloon at its distal end. The balloon is inflated to retain the feeding tube inside the stomach. The sheath is then peeled away, leaving behind the feeding tube. In addition, this feeding technique is cumbersome to utilize and requires multiple steps in addition to the step of direct insertion of a T fastener. Also, the number of punctures, are increased, resulting in higher probabilities of infections and failures. As the introducer is peeled off, there is a risk of air leaking.

Many attempts have been made to make percutaneous gastrostomy simpler. Iwatschenko, in U.S. Pat. No. 4,834,725, describes a catheter for introduction through the abdominal wall into the gastric lumen where it is secured against slipping out of the stomach of its end by a portion of a catheter assuming a spiral configuration in the interior of the stomach and resting on the stomach wall upon withdrawal of a trocar. With this method, the inner portion of the catheter can be easily pulled out by the patient because any upward pulling would uncoil the inner part of the G tube. This method also runs the risk of trauma to the stomach wall and increased G tube clogging, due to the long, spiral shape of the intra-gastric part of the tube.

As described in U.S. Patent Publication No. 2007/0016172, a tapered dilator feeding tube portion aids in allowing the gastrostomy feeding tube to pass through the stoma and once the tube has been properly positioned with the end cap snug against an internal wall of the stomach, after the dilator portion of the feeding tube is cut away, a rubber bumper, also known as an external retention member, is prepared and positioned on the feeding tube as it emerges from the abdominal wall, and once the feeding tube is secured in place, a Y-port adapter is connected to it. These additional steps add complexity. Furthermore, the dilator needs to be cut away in this method. This procedure runs the risk of requiring re-scoping the stomach to confirm successful placement and enhances the risk of infection and carrying malignant cells from the mouth and esophagus to the peritoneal space, as with other inside out procedure.

Ross in U.S. Pat. No. 6,015,400, describes a method for placing a feeding tube unit, which involves placement of a dilating device having a proximal end portion and a distal end portion and positioning a feeding tube unit defining a channel such that a distal end portion of the feeding tube is positioned within the channel defined through the dilating device and the feeding tube is urged into a gastrointestinal tract of a patient followed by removal of the dilating device. However, there is a possibility of leaks occurring through this method.

Also, Gastrostomy tube percutaneous insertion kits are known, such as the Kimberly-Clark™ Introducer Kits, a class II medical device. Such kits include a gastropexy, a dialtor with a peel-away sheath, a syringe, a hemostat, an introducer needle, a seeking catheter, a scapel, a guidewire and a stoma measuring device, for example. In one example, a kit is intended to facilitate the primary placement of a gastrostomy feeding tube. In another example, a different kit is intended to facilitate primary placement of a transgastric jejunal feeding tube using endoscopic/radiologic placement. A transgastric jejunal feeding tube is known that uses a balloon on a stylet with a diameter of 22 centimeters and a length of 45 centimeters and a volume of 7-10 milliliters, which is used for pulling or pushing the transgastric jejunal feeding tube to a jejunal location. Both the gastrostomy tube and the jejunal tube may be fixed in place using a bolster.

In one known example, a combination of transgastric jejunal feeding tube and a gastrostomy feeding tube is provided. The jejunal feeding tube may be inserted through the lumen of the gastrostomy feeding tube. A Y-port connector end of the jejunal feeding tube may be pressed into the lumen of the gastrostomy tube to complete placement and to allow for gastric drainage through the gastrostomy tube. A combined gastrostomy tube and jejunal feeding tube is an improvement over separate gastrostomy tubes and jejunal tubes, which require removal of the gastrostomy tube prior to inserting a jejunal tube, but the combined gastrostomy tube has complications and requires a multi-part Y-port connector end to be positioned and retained in the lumen of the gastrostomy tube. A Bard™ Tri-Funnel Replacement Gastrostomy Tube has a concentric balloon collar a the end inserted into the stomach that minimizes the potential for accidental removal of the clear silicone feeding tube and an adjustable bolster is used externally opposite of the concentric balloon to fix the gastrostomy tube in the patient's stomach. It is a simple device that provides a balloon collar at one end of the gastrostomy feeding tube and is designed to be a replacement tube.

All materials of such devices that come into direct contact with the patient have a history of use in medical devices and are biocompatible, sterile and functionally safe and effective for use in humans. However, insertion and removal may cause infection and complications, nonetheless, due to contamination during insertion, positioning or use of prior art gastrostomy tubes, jejunal tubes or combination gastro-jejunal tubes.

SUMMARY OF THE INVENTION

An improved gastrostomy tube and an improved combination of a gastrostomy tube and jejunal tube reduces complications and improves patient outcomes compared to known prior art devices. For example, an integrated gastro jejunal tube unit has a jejunal tube with a jejunal tube outlet port and has a gastric sleeve. The sleeve may be a tube capable of sealingly fitting over a jejunal tube, for example. A jejunal balloon collar includes a balloon that is extendable outwardly from the jejunal tube. The balloon collar of the jejunal tube may be disposed at or near an end of the jejunal tube that extends into the gastrointestinal tract. For example, the balloon collar may surround the jejunal tube and may be inflatable, extending radially outwardly from the jejunal tube. The jejunal balloon collar may be in fluid communication with an inflation port. For example, inflating the jejunal balloon collar by air or liquid delivered through the inflation port may be used to block a portion of the intestinal tract. Drainage holes may be disposed along a portion of the jejunal tube. In one example, the drainage holes in the jejunal tube start at or near a jejunal balloon collar and extend in a direction away from the end of the jejunal tube.

When inflated to at least partially block fluid communication with the lower GI tract, fluids collecting in the intestinal tract may be drained through drainage holes disposed through a surface of the jejunal tube. No known jejunal tube has a balloon capable of being retained in the jejunum during jejunal feeding. The only known device includes a balloon only on a stylet that is used temporarily for placement of the jejunal feeding tube. Then the balloon is removed together with the stylet. In one example, the balloon prevents both the fluid from continuing along the intestinal tract and closes the end of the jejunal tube, such that suction or gravity may be used to drain the fluids. In another example, the drainage holes are in fluid communication with a channel or an annular region of the jejunal tube that may or may not be in fluid communication with a central channel of the jejunal tube that delivers nutrition to the patient. In one example, nutrition may be delivered from the end of the jejunal tube at the same time that fluids are removed from the intestinal tract on the opposite side of a jejunal balloon collar. In another example, a jejunal balloon collar is inflated to properly position the jejunal tube within a portion of the GI tract, but the jejunal balloon collar does not block the path of digesting food and fluids from passing beyond the jejunal balloon collar when inflated at least partially. For example, inflating with 10-20 milliliters of a saline may be used to properly position the jejunal tube.

In one example, a feeding tube comprises a gastric tube having a central channel and a feeding inlet; a gastric balloon expansion inlet at a first end of the gastric tube; a gastric balloon in fluid communication with the gastric balloon expansion inlet and disposed distal from the gastric balloon expansion inlet such that the gastric balloon expands in volume when a volume of fluid is injected into the gastric balloon expansion inlet; and an insertion device extendable through the central channel of the gastric tube and having a protective collar extendable over the gastric balloon or a second balloon such that the gastric balloon or the second balloon is at least temporarily protected from damage during insertion of the feeding tube in the gastrointestinal tract. For example, the first balloon is disposed at a distance from the end of the first tube, and the gastric tube includes holes extending through the thickness of a portion of the gastric tube disposed between the gastric balloon and an opposite end of the gastric tube disposed opposite of the first end of the gastric tube.

In an integrated gastrostomy tube and jejunal tube, the jejunal tube is extendable through the central channel of the gastric tube and has a jejunal channel along a length of the jejunal tube such that the insertion device is extendable through the jejunal channel and the central channel of the gastric tube to assist with insertion of the jejunal tube and the gastric tube in the gastrointestinal tract. In one example, the jejunal tube comprises a jejunal balloon expansion inlet at one end of a jejunal balloon expansion channel and the second balloon at an opposite end of the jejunal balloon expansion channel, such that the second balloon is in fluid communication with the jejunal balloon expansion inlet via the jejunal balloon expansion channel. For example, the protective collar extends over the second balloon such that the second balloon is at least temporarily protected from damage during insertion of the feeding tube into the gastrointestinal tract. The expansion of the jejunal balloon permits the insertion device and the protective collar of the insertion device to be removed from the jejunal tube in one example. The expansion of the jejunal balloon results in segmentation of the protective collar along tear lines between the segments. And in one example, the protective collar is comprised of overlapping segments, and the overlapping segments are not attached along at least a portion of a length of the overlapping segments.

In one example, the jejunal balloon is capable of expanding to block off a portion of the jejunum, when the jejunal balloon is expanded by injecting a first volume of fluid into the jejunal balloon, and in another example, the jejunal balloon is capable of blocking a central outlet from a tip of the jejunal tube, when the jejunal balloon is expanded by injecting a second volume of fluid into the jejunal balloon. The jejunal tube may have a loop extending from a tip of the jejunal tube, and a clip may be used to secure the loop and the tip of the jejunal tube within the gastrointestinal tract. In one example, gastric tube and the jejunal tube form an annular cavity or at least one channel disposed between the gastric tube and the jejunal tube. When the gastric tube and the jejunal tube form an annular cavity disposed between the wall of the gastric tube and the wall of the jejunal tube, holes extending through a thickness of the gastric tube at a second end of the gastric tube, opposite of the first end of the gastric tube, are in fluid communication with a drainage outlet disposed proximally to the first end of the gastric tube, allowing drainage to a drainage bag and gastric decompression.

In one example, a protective collar is extendable over the gastric balloon. In an alternative example, the protective collar is extendable over a second balloon, and the second balloon is disposed at a second end of the gastric tube opposite of the first end of the gastric tube. For example, the volume of the second balloon may be greater than twenty milliliters. The gastric tube may include holes extending through the thickness of the gastric tube at a second end of the gastric tube opposite of the first end of the gastric tube. In one example, the gastric tube includes an integrated bolster fixed on the gastric tube and extending outwardly from a circumference of the gastric tube. The gastric tube includes a balloon collar disposed relative to the gastric balloon such that the gastric balloon is deflected by the balloon collar in the direction of integrated bolster causing the gastric balloon and the integrated bolster to develop a clamping force between the gastric balloon and the integrated bolster.

In another example, nutrition exiting the outlet port of the jejunal tube is prevented from backing up the GI tract by the jejunal balloon, and any surgical incisions or resections on the opposite side of the balloon from the outlet are unaffected by the delivery of nutrition by the jejunal tube. Thus, a patient may safely receive nutrition jejunally soon after completion of a surgical procedure, which may surprisingly improve patient recovery and reduce hospital stays. In one example, the gastro-jejunal tube may be attached to a drainage bag to allow for passage of intestinal contents from the gastro-jejunal tube to the drainage bag.

In one example, the drainage holes through the surface of the jejunal tube are in fluid communication with a central tubular orifice of the jejunal tube. Thus, any blockage of the central tubular orifice is bypassed by flow through the drainage holes. In this example, the "drainage" holes may be used as feeding holes in addition, to be used as drainage holes. During administration of nutrition, nutrients may be directed through the jejunal tube through either or both of the orifice at the end of the jejunal tube and the drainage holes. During drainage, fluids may be drained through the drainage holes and/or the orifice to a drainage (or colostomy) bag.

A gastric sleeve may form an annular sheath around a portion of the jejunal tube. A gastric balloon collar may be disposed on the outer surface of the gastric sleeve. Gastric drainage holes may be disposed in the annular sheath of the gastric sleeve to extract fluids using a suction port. The gastric drainage holes may be disposed between the end of the gastric sleeve that is inserted into the gastrointestinal tract and the gastric balloon collar. The balloon collar of the gastric sleeve may be used to seal the gastric sleeve in the intestinal tract, similar to the integrated tube disclosed in U.S. Provisional Patent Application No. 61/031,442, filed Feb. 26, 2008, the specification and drawings of which are incorporated herein by reference in its entirety. A gastric balloon expansion port is in fluid communication with a channel such that gas or liquid may be used to inflate the gastric balloon of the gastric balloon collar. The gastric balloon may be inflated outwardly from the gastric tube and may be deflated when removal of the integrated gastro jejunal tube unit is desired.

In another example, the gastric sleeve may be used as a gastrostomy feeding tube with or without insertion of the jejunal tube. With insertion of the jejunal tube, feeding may be accomplished through the jejunal tube and drainage may be accomplished through the annular region between the gastric sleeve and the outer wall of the jejunal tube. Alternatively, the gastrostomy tube may be used without a jejunal tube for gastric feeding, when feeding in the upper gastrointestinal track is indicated, and a jejunal feeding tube may be inserted when feeding in the upper gastrointestinal track is contraindicated, such as after post upper, GI tract surgery, radiation therapy, chemotherapy, reflux and other conditions associated with nausea, vomiting and possible aspiration.

In one example, a fixation device is disposed at or near the end of the jejunal tube. For example, the fixation device may be a black silk loop attached to the end of the jejunal tube.

Surprisingly, a gastro jejunal tube unit having drainage and suction may be used to deflate or inflate the stomach. Also, a jejunal tube may use the inflatable collar to provide nutrition very soon after surgery, without risk of leakage from a resection, for example, dramatically reducing recovery time and improving outcomes for patients by maintaining nutritional health and bowel functions.

In one example, a constant internal endoscopic visualization of the procedure provides greater control and reduces uncertainty compared to methods requiring removal of the endoscope from the insertion site. Unexpectedly, repeated insertion and withdrawal of the endoscope and gastric/jejunal tube is not required, as it is for other known systems, reducing complications, such as perforation of the esophagus and bleeding associated with repeatedly inserting an endoscope. Instead, the entire procedure for insertion is accomplished under constant endoscopic visualization, for example.

Still another advantage is that feeding may be initiated through the gastric sleeve outlet port or the jejunal tube outlet port, depending on the clinical state of the patient, and thereby avoiding any needless reinsertion or feeding through a total parenteral nutrition method, for example, when normal gastric functioning cannot occur.

In one example, an integrated tube unit comprises an external feeding tube having a balloon collar on one end of the tube, a first channel extending along the feeding tube for feeding, a second channel for inflating the balloon collar, and an internal insertion device. For example, the insertion device, is a temporary dilator that fits inside the external tube and is subsequently removed from the external tube. In contrast to conventionally known procedures of inserting a feeding tube, the integrated tube unit may be done entirely under endoscopic visualization.

In one example of the method, an endoscope has a snare which comprises a loop capable of being extended and withdrawn, such that a tube, needle, or wire may be retained by the snare, when the snare is pulled taut, The endoscope utilized in the method has the ability to fill a stomach with air, and includes a light, and fiber optics for viewing inside the stomach. The endoscope is one utilized by a person of ordinary skill in the art and may include well-known endoscopes produced by Olympus® and Pentax® for example.[1] In a first step, the endoscope is inserted down the esophagus and to the stomach of the patient. The endoscope is then extended to the abdominal wall near the stomach, and is used to fill the stomach with air, displacing viscera between the stomach wall and the abdominal wall. The endoscope light is used to identify the location of the endoscope, which may be felt using a finger of a surgeon's hand, also. Once the endoscope in the stomach is positioned and identified, an incision is made through the skin and fat above the location of the endoscope. The abdominal muscles may be then split to permit the entry of a needle and a sheath through the stomach wall. The needle is then withdrawn. A guide wire is then inserted through the sheath and into the stomach. The endoscope is used to see the location of the guide wire, as it is inserted into the stomach, and the snare of the endoscope is used to capture the end of the wire. The sheath may be removed once the guide wire is secured by the snare of the endoscope.

[1] Olympus® is a registered trademark of Olympus Corporation, Japan; Pentax® is a registered trademark of Pentax Corporation, Japan.

Over the guide wire, an integrated tube unit may be introduced. The integrated tube unit comprises an external tube and an internal insertion device. While viewing the point of insertion with the endoscope, which is not removed, the integrated tube unit, is pushed along the guide wire into the stomach, puncturing the stomach wall, and thus into the stomach through the punctured opening in the stomach wall. The internal insertion device extends through the first channel extending along the external feeding tube for feeding, and beyond the end of the external feeding tube. The insertion device has a pointed end extending from the external feeding tube, which acts as a dilator and an internal channel for following the guide wire.

While guiding the integrated tube unit along the guide wire, the pointed end of the insertion device (i.e., the dilator end, for example) is inserted into the incision and the punched hole through the stomach wall, expanding the hole, and allowing insertion of the integrated tube unit into the stomach. A protective sheath may extend upwards from a portion of the dilator end of the insertion device, such that the external feeding tube and the balloon collar are protected during insertion of the integrated tube unit. Then, the balloon collar is expanded, via a port in the integrated tube unit, for example. In one example, expansion of the balloon collar, which is expanded to provide a seal at a point of insertion of the external feeding tube, also displaces the protective sheath, (if a sheath is used), outwardly from the pointed end of the insertion device.

Then a bolster may be slipped down the shaft of the external feeding tube to securely affix the external feeding tube. The bolster may be secured in place by friction, a clamp, or sutures to affix the abdominal musculature and stomach wall between the balloon collar and the bolster. Thus, the hole pierced in the stomach is sealed by the external tube, which may be used as a feeding tube, for example. The dilator may be removed from within the external feeding tube, when the guide wire is removed. In one example, the guide wire is removed after the dilator is removed. Alternatively, in another example, the guide wire may be removed at the same time that the dilator is removed. Then the external feeding tube, which extends from a location external to the patient through the skin, fat, musculature and stomach wall and into the stomach, may now be used for feeding the patient. For removal of the feeding tube, the balloon collar is deflated and then the feeding tube is removed from the stomach.

In one example of using the integrated tube unit, the integrated tube unit may be used to assist in weight loss. The integrated tube unit is placed in the same way, but the purpose is to expand the balloon collar, to reduce the capacity of the stomach and thus create a sense of fullness to the patient undergoing treatment. Occasionally, for example, the integrated tube unit may utilize scanning guidance such as CAT scan guidance, for example in certain situations. For example, the patient may have a very thick subcutaneous fat layer, thus making it more difficult to localize the integrated tube unit through the point of insertion.

In one specific example of the method of inserting an integrated tube unit, the steps comprise: inserting an endoscope, insufflating a stomach of a patient, choosing a site for insertion of the integrated tube unit, which includes a gastrostomy tube (G-tube); making an incision at a chosen site; inserting a snare through the endoscope and leaving the snare in the open position in the stomach activity, inserting an angiocath through the incision; placing the open snare around the angiocath and closing the snare; removing a needle stylet from the angiocath; passing a guide wire through the angiocath and securing the guide wire through the snare; removing the angiocath, leaving behind the guide wire held by the snare; inserting an integrated tube unit having a inner dilator with a protective collar and the external G tube; sliding a disk over the integrated tube unit in order to create a pull force at the top of the dilator; pulling the guide wire while simultaneously pushing the dilator, placing the G tube in the stomach cavity; inflating a balloon at one end of the G tube inside the stomach with saline or other fluid; gently pulling the G tube, loosening the guide wire by opening the snare loop, and pulling the guide wire from the feeding tube, securing the G tube against an inner wall of the stomach; loosening the disk over the dilator and pulling the dilator out; loosening the guide wire by opening the snare loop and pulling the guide wire from the G tube, and applying an external bolster for further securement of the G tube to the abdominal wall by sliding the external bolster down the G tube, leaving only the G tube and bolster in place.

A system for feeding tube insertion, in one example, includes an endoscope, a snare and a guide wire, an angiocath, an integrated tube unit having a dilator with a protective collar and a feeding tube; a disk, and an external bolster.

In one example, a portion of the dilator is within the feeding tube, although the dilator end extends from the distal end of the feeding tube by a small amount and the collar covers the end of the G tube and a balloon. In one example, the small amount is about ½ inch or 1.27 cm. The dilator tip may have a flexible collar that extends back up the outer side of the feeding tube by ½ inch, for example. For example, the dilator and its flexible collar form a single unit. The single unit may be formed from a flexible plastic material, such as a polyurethane, a polyethylene, a polyvinyl, a nylon, a silicone rubber, a co-polymer, a PTFE or the like. By having only a minimal portion of the flexible collar extending over the feeding tube's distal end, the feeding tube is prevented from being held up at the dilation entry point. In addition, this unit prevents a larger dilation entry point into the stomach than necessary to fit the external tube. One advantage of the dilator of the integrated tube unit is that this prevents larger entry points than required for a feeding tube or other purpose, as distinguished from methods requiring larger entry points because the dilator must be positioned outside of the feeding tube.

Yet another advantage is that displacement of bacteria or cancer cells may be reduced, unlike previous methods which involved pulling of the feeding tube through the mouth without endoscopic visualization. Another advantage is that removal and replacement of the jejunal tube is also simplified, as the jejunal balloon collar may be deflated and the tube pulled out through the gastric sleeve. Also, using a gastrocutaneous fistula, a new external tube may be placed within the stomach. Another advantage is that the time for completion of the procedure is reduced, as compared to a surgical insertion procedure, such as the method used in the total parenteral nutrition method, for example.

The integrated gastro jejunal unit is much more easily inserted and replaced, compared to conventional jejunostomy feeding tubes. According to a method of replacement, either the jejunal tube only or both the jejunal tube and the gastric tube may be replaced by deflating a balloon collar for easy removal.

BRIEF DESCRIPTION OF THE FIGURES

FIG. 7B-7F include additional examples and details of examples of an introducer dilator insertion device useful in a method of inserting a gastrostomy feeding tube and/or an integrated gastro jejunal feeding tube.

FIG. 9 illustrates an example of a step of introducing the integrated gastro jejunal tube unit.

FIG. 10 illustrates another step in a method of introducing the integrated gastro jejunal tube unit.

DETAILED DESCRIPTION

The examples described and the drawings rendered are illustrative and are not to be read as limiting the scope of the invention as it is defined by the claims that eventually issue.

Figure 1:
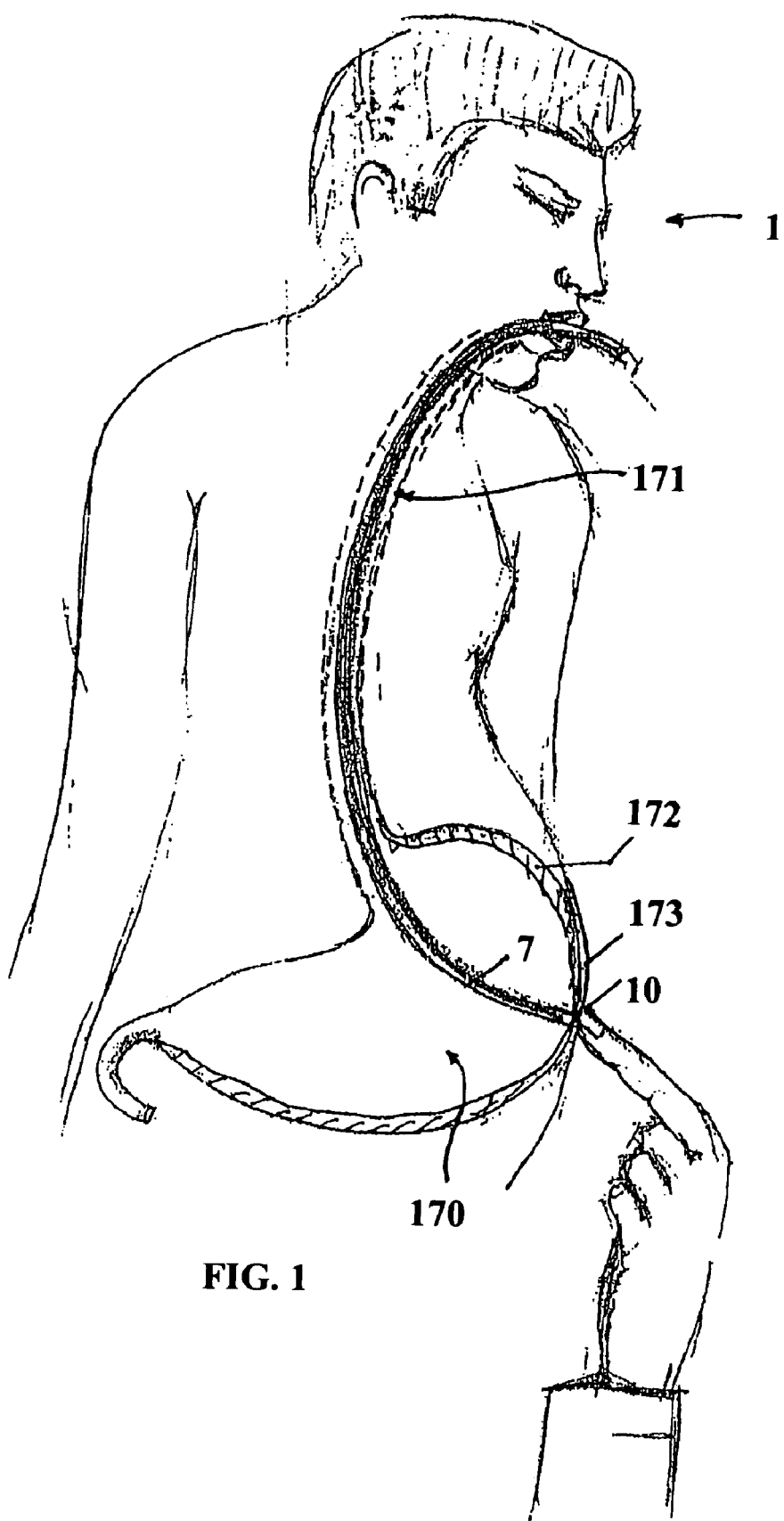
FIG. 1 is a schematic representation of an example of a step of preparation for a method of inserting an external tube.

In FIG. 1, the endoscope 7 is disposed adjacent to the abdominal wall within the stomach and is used to fill the stomach with air, displacing viscera between the stomach wall 172 and the abdominal wall 173. The light on the endoscope may be used to identify the location of the endoscope, which may also be felt using a finger of a surgeon's hand, as illustrated in FIG. 1. For example, a physician may use finger pressure at a position 10 to locate a site for insertion of an external tube such as a gastrostomy tube. Once the location of the endoscope in the stomach is confirmed, by whatever means, the physician may transluminate the abdominal wall of the patient with an endoscope light, and may select a site to insert the feeding tube.

Then, a small incision may be made by the physician at the site. After an appropriate anesthetic is applied, an incision may be made through the skin and fat above the location of the endoscope, The abdominal muscles may be split or cut to permit entry of a needle, such as an 18 gauge, 17 centimeter needle, as used in Russell percutaneous endoscopic gastronomy procedures. As is known in the art, a sheath may be extended through the stomach wall, puncturing the stomach without release of air pressure using the Russell percutaneous endoscopic gastronomy procedure. A Foley catheter may be inserted as described by Robert E. Miller, M.D., et al. in *Gastrointestinal Endoscopy*, v. 34, no. 4, pages 339-342 (1988), which describes inflation of a balloon of a lubricated 14F Foley catheter with 6 millileters of saline.

Figure 2:
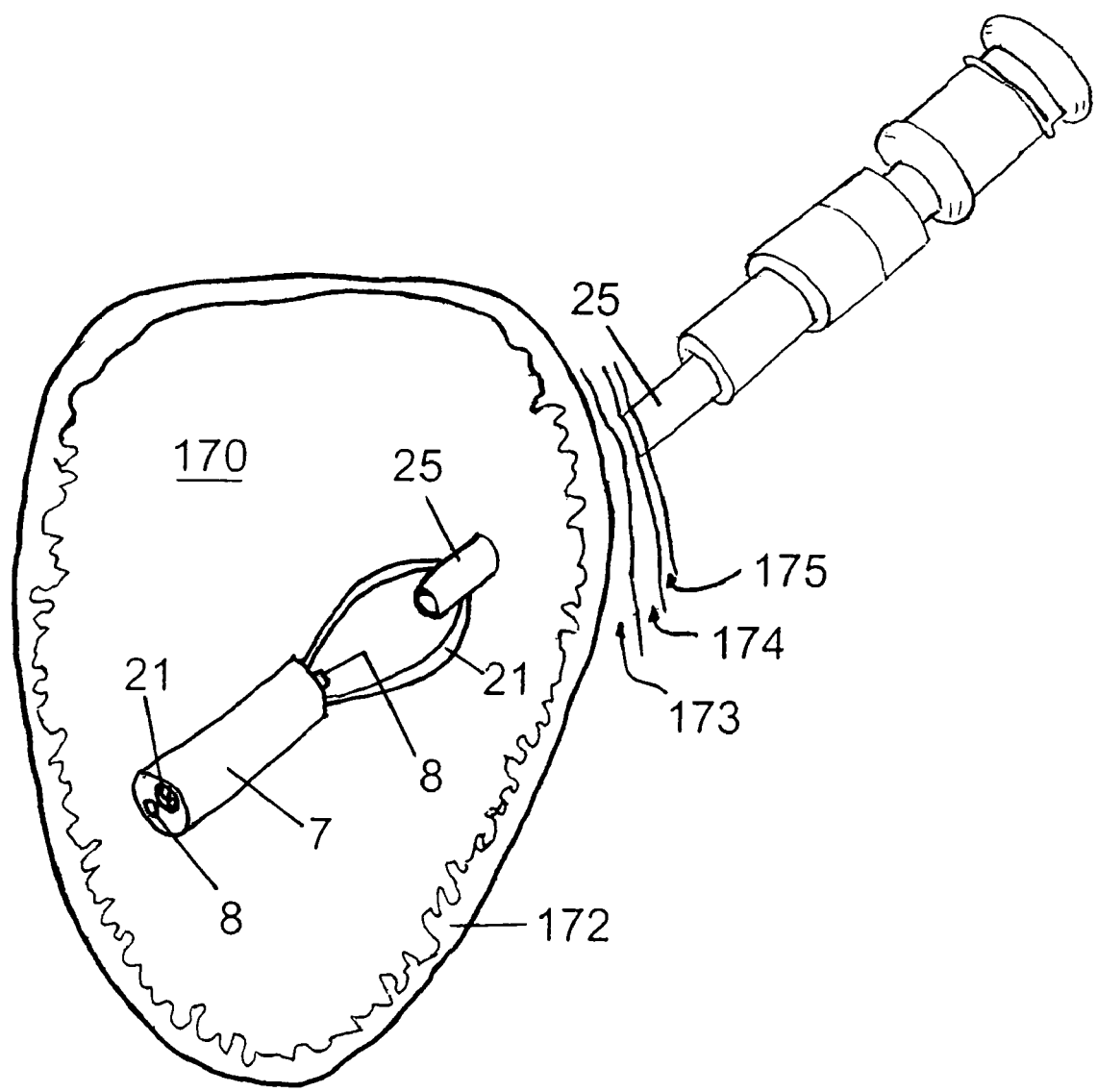
FIG. 2 illustrates another step of a method of inserting an external tube.

In one example of the present invention, the size of the incision may be 10-15 mm or more. The incision should be deep enough to break through the subcutaneous tissue. The physician should make sure that the stomach is sufficiently inflated to avoid insertion of instruments through other organs than the dermis 175, fat 174, muscle 173 and stomach wall 172, as shown in FIG. 2. Other methods, other than inflation, may be used by a person of ordinary skill in the art to avoid piercing of other organs.

Endoscopes are known in the art that use fiber optics 8 and/or lenses for viewing inside the GI tract. Endoscopes have various tools that may be inserted through the endoscope. An endoscope may be used to inflate the stomach cavity 170, as is known in the art. Such well-known endoscopes include endoscopes produced by Olympus® and Pentax® for example.[2]

[2] Olympus® is a registered trademark of Olympus Corporation, Japan; Pentax® is a registered trademark of Pentax Corporation, Japan.

A snare may be inserted via the endoscope. As shown in FIG. 2, a snare 21 is left in the open position in the stomach cavity at the feeding tube site of insertion. One example of a snare is a Boston Scientific® Sensation™[3] polypectomy snare with a UPN product number of M00562690. The physician, uses the endoscope 7, to advance an angiocath 25 through the incision and into the stomach cavity. The snare 21 in the open position may be placed around the angiocath 25 and then retracted, holding the angiocath 25 gently. A needle stylet may be removed from the angiocath by gently pulling the needle stylet while pulling the angiocath 25 with the snare 21, for example. All the while, the physician may observe the angiocath 25 with the fiber optics 8 of the endoscope 7. Alternatively, instead of fiber optics 8, a lens may be used, for example.

[3] Boston Scientific® and Sensation™ are trademarks of Boston Scientific.

Figure 3:
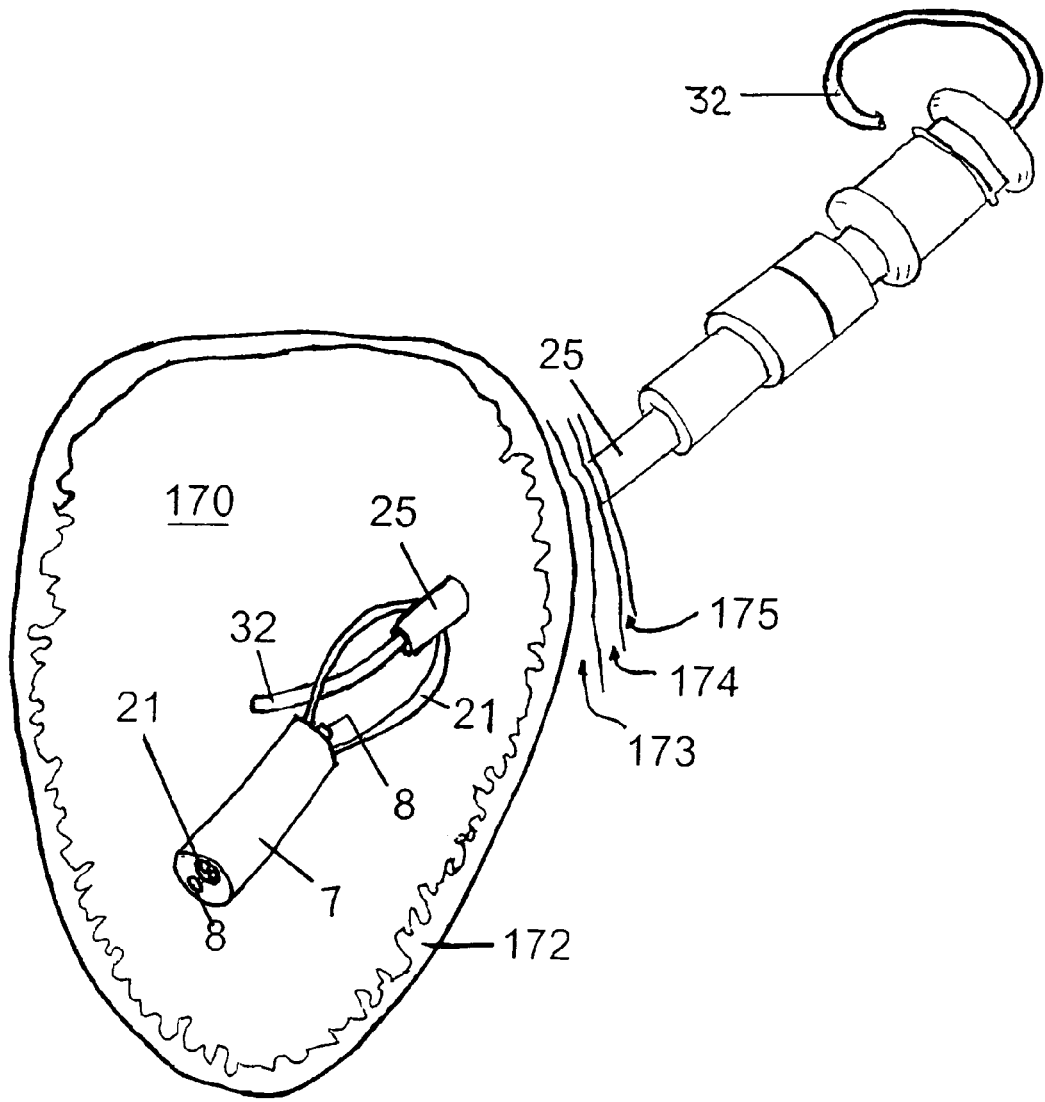
FIG. 3 shows another step of a method of inserting an external tube.

In FIG. 3, the snare 21 is opened when a guide wire 32 is passed into the stomach cavity 170 through the angiocath 25. Then, the guide wire may be held by retracting the snare 21 around the guide wire 32. In one example, a guide wire 32 may be inserted through a sheath, such as a tear away sheath, into the stomach. An endoscope 7 is used to see the location of the guide wire 32 as it is inserted into the stomach, and a snare 21 of the endoscope 7 is used to capture an end of the wire 32. If a sheath is used, the sheath may be removed once the guide wire is secured by the snare of the endoscope, for example.

The ability to continuously view the guide wire 32 and the insertion procedure internally by the endoscope 7 and externally by direct observation of the surgical team is a significant advantage, providing better control, and a more precise placement within the stomach than other procedures that do not use an endoscope for continuous observation.

Figure 4:
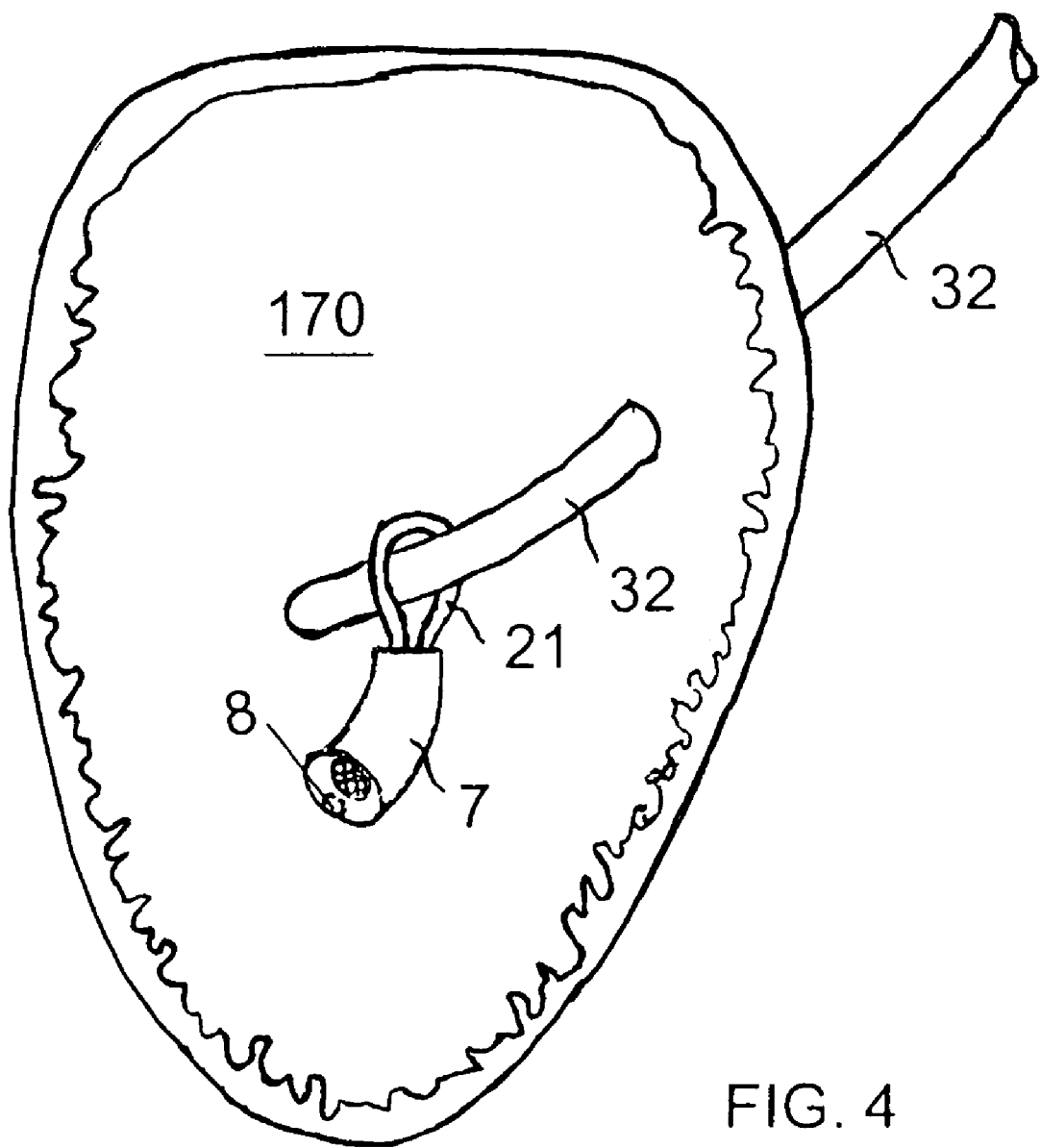
FIG. 4 depicts another step of a method of inserting an external tube.

The angiocath 25 (or sheath or sleeve) may be removed, leaving behind a guide wire 32 held by a snare 21 in the stomach cavity 170, as shown in FIG. 4, for example. Again, pulling of the angiocath 25 may be counterbalanced on the guide wire 32 by pulling on the guide wire 32 using the snare 21 of the endoscope 7. An introducer dilator 77 is shown as inserted through a jejunal tube 50 in FIG. 5. The introducer dilator 77 may extend beyond a jejunal tube 50 at one end of the jejunal tube and may have a protective extension 71 at an opposite end of the jejunal tube 50 that is capable of protecting a balloon 68, such as an inflatable annulus or collar, at the end of the jejunal tube 50 that extends into the stomach cavity 170 during insertion of the jejunal tube 50. The protective extension 71 may be made of a flexible materials, such that the introducer dilator 77 may be removed following insertion by pulling the protective extension 71 back through the jejunal tube 50, for example. Alternatively, the protective extension 71 may be partially or completely capable of breaking away from the dilator 77 such that the dilator 77 and/or at least a portion of the extension 77 may be withdrawn from the jejunal tube 50. In one example, the protective extension 71 is made of a material capable of dissolving over time when placed in the GI tract 170.

Figures 5, 6:
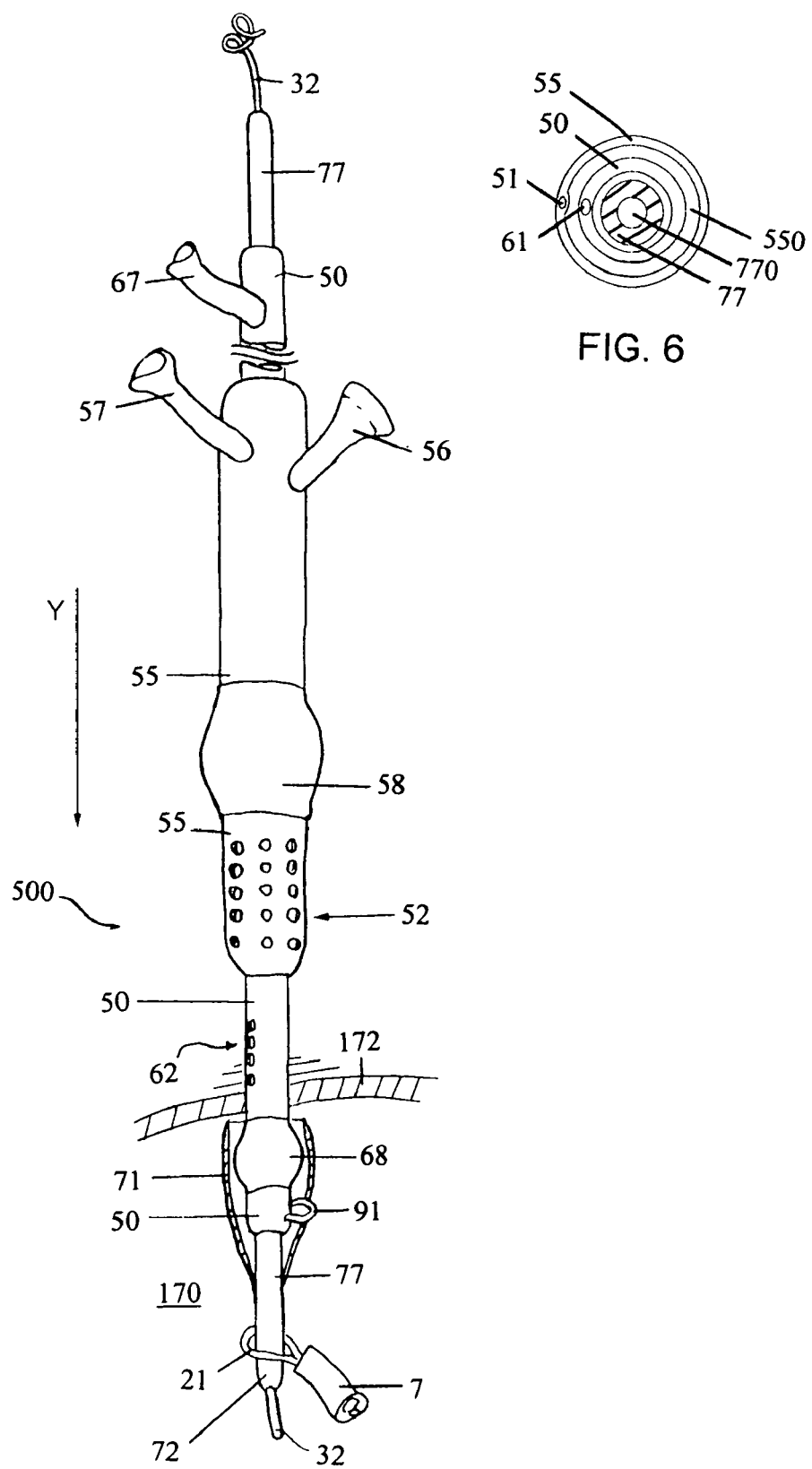
FIG. 5 illustrates an example of a step of a method of inserting integral gastro jejunal feeding tube and an example of an integral gastro jejunal feeding tube having an introducer dilator and a partial cross sectional view of a protective shield of the introducer dilator covering a jejunal balloon collar in its deflated state.
FIG. 6 illustrates an example of a radial cross section view of one example of the integral gastro jejunal feeding tube of FIG. 5.
Figure 11:
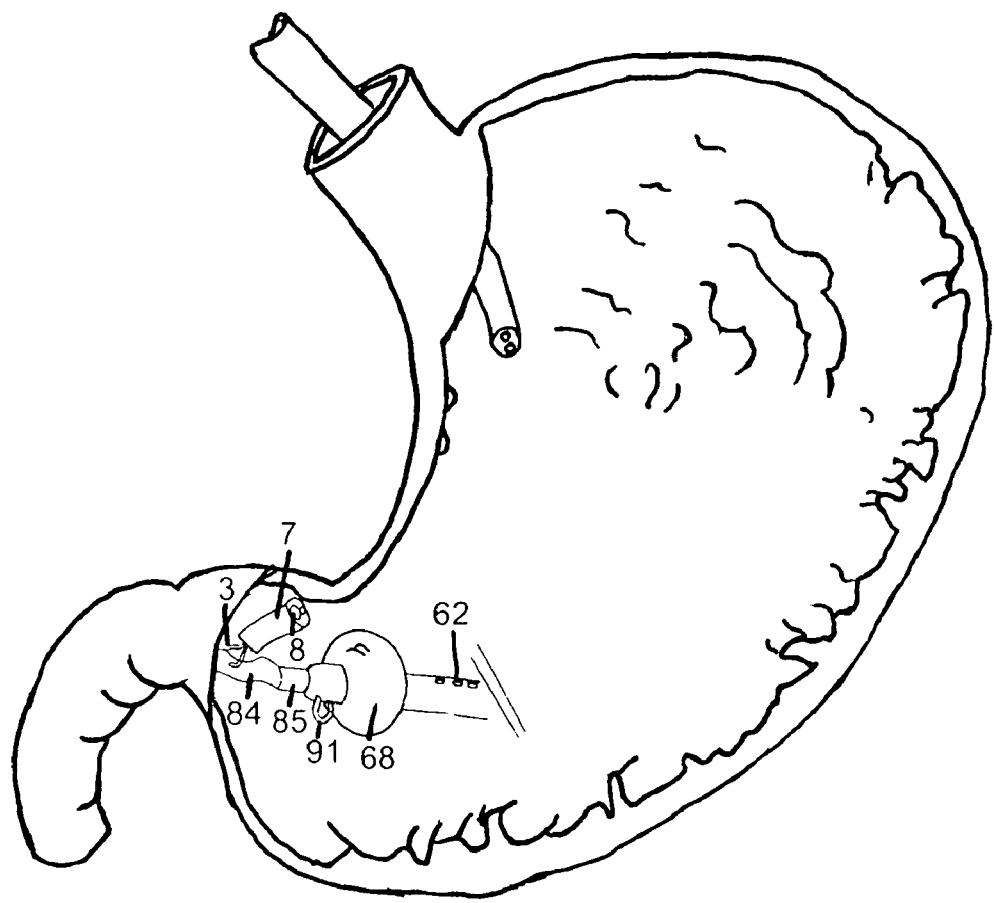
FIG. 11 illustrates another step in a method of introducing the integrated jejunal tube unit.

As illustrated schematically in FIG. 5, a jejunal tube 50 with an inserted introducer dilator 77 may be inserted into the stomach over a guide wire 32, which passes through the dilator 77. Then, the jejunal balloon 68 may be inflated, as illustrated in FIG. 11, for example, while the dilator 77 is withdrawn from the stomach cavity 170. Thus, an end of the jejunal tube 50 is inserted into the stomach cavity 170 under constant endoscopic visualization. As illustrated schematically in FIGS. 14B-C, a jejunal tube 50 may extend into and may have a loop 91 fastened by a clip 103 to the lining of the jejunum. In one example, the jejunal tube 50 extends a length in a range from about 4 centimeters to no greater than 200 centimeters beyond an end of the gastric sleeve 55.

FIG. 5 shows an example of an integrated gastro jejunal tube assembly 500 with an introducer dilator 77 inserted, just before fully inserting the gastric tube 55 into the stomach cavity 170. In one alternative embodiment, the integrated gastro jejunal tube assembly 500 is sufficiently rigid with only a guide wire 85 and no introducer dilator 77 is introduced. An integrated gastro jejunal tube unit 500 may be introduced over a guide wire 32, 85, such as a J wire, which is being held by the endoscope 7, for example. While the endoscope 7 is viewing the point of insertion, the integrated gastro jejunal tube unit may be pushed through the incision along the guide wire 32 and into the stomach cavity 170. A rotational back and forth motion may be used to prevent the unit from kinking a guide wire 32, 85, for example. Various fittings 56, 57, 67 may be provided on the gastric jejunal tube unit 500 to provide for balloon 58, 68 inflation and drainage through drainage holes 52, 62 such as illustrated schematically for a gastric sheath 55 in FIG. 5 or in more detail in the integrated gastro jejunal tube unit 500 of FIG. 6A.

For example, a balloon expansion port 57, 67 may be provided for inflating of a balloon collar 58, 68 for either or both of the gastric sleeve 55 and the jejunal tube 50. A drainage port 56 may extend from on end of the gastric sleeve 55 and may be in fluid flow communication with drainage holes 52 formed through an end of the gastric sleeve 55 that extends into the stomach cavity 170. A jejunal feeding port 66 may provide access for nutrition, when feeding, and for drainage when not feeding. The integrated gastro jejunal tube unit 500 of the example in FIG. 5 and FIG. 6 comprises a jejunal tube 50 which extends annularly into a gastric sleeve 55 forming an annular cavity 550. The gastric sleeve 55 is as an outer tube annularly enclosing a portion of the jejunal tube segment 65. The gastric sleeve 55 may terminate in a region just below gastric drainage holes 52, for example. In one example, the sleeve 55 forms an annular region around the jejunal tube 50 and may extend up to about 20 cm into the stomach 170. A gastric balloon 58 may be disposed annularly around the gastric sleeve 55 and may be at a distance of about 5 centimeters from the end of the gastric sleeve 55, for example. Each of the gastric balloon collar 58 and the jejunal balloon collar 68 may extend a length of about 1 centimeter along the surface of the gastric sleeve 55 and the jejunal tube 50, respectively, for example. Gastric drainage holes 52, 62 may be used to drain gastric contents during a post-operative period, gastric decompression or may be used as inlets for feeding and/or medicine, for example.

Figure 7A:
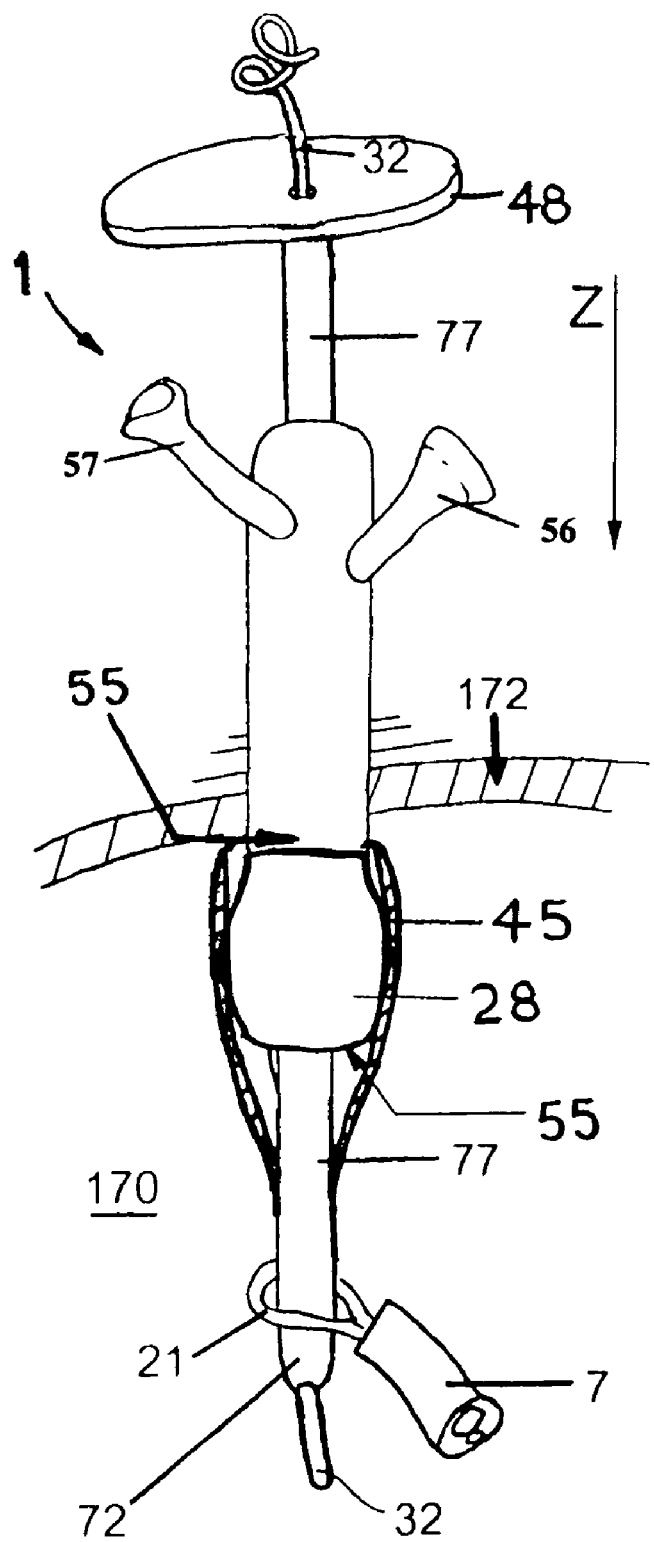
FIG. 7A illustrates an example of a gastrostomy feeding tube being inserted using an introducer dilator and a partial cross sectional view of a protective shield of the introducer dilator covering a gastric balloon in its deflated state.

In one example, such as illustrated in FIG. 7A, a disk 48 may be slid down the guide wire 32 to create a force against the top of the dilator 42, as illustrated in FIG. 7A. In this example, the disk 48 is slid through a central hole for guide wire 32 passage. In an additional example, the disk 48 may have additional hooks or may use other devices to lock the disk 48 to the wire 32.

Figure 7D:
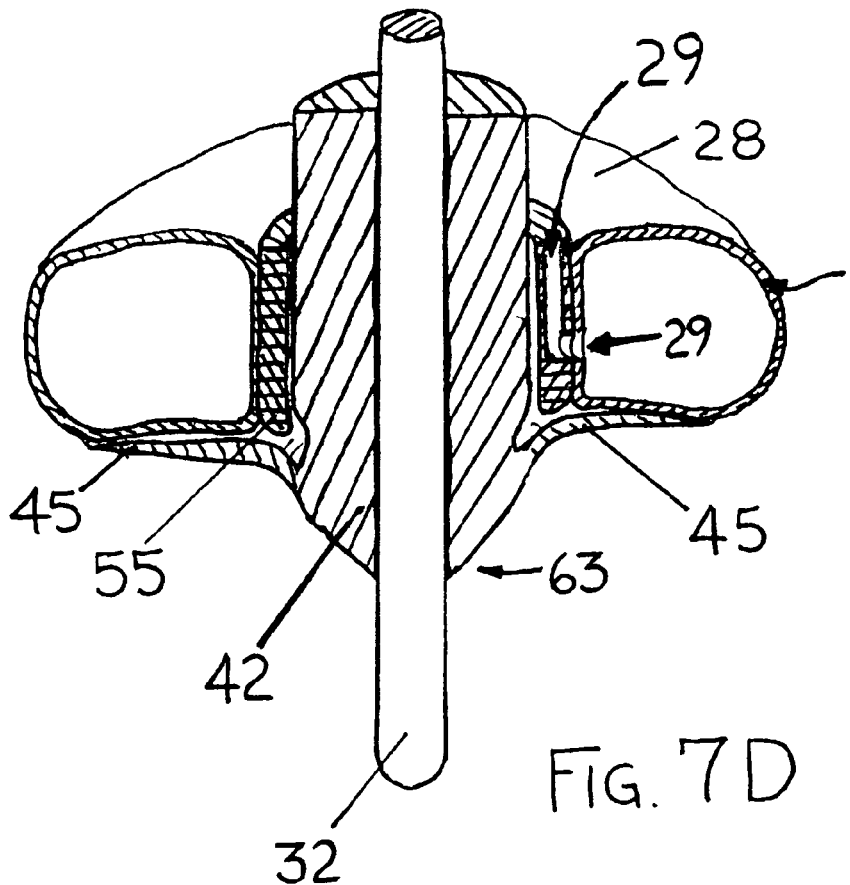

The integrated tube unit 1 of the examples in FIGS. 7A-7F comprises an external gastrostomy tube 55 having an inflatable collar 28, and an internal dilator 77, 42 having a dilator tip 72, 63, a through-hole 171 for accommodating the guide wire 32 and a protective collar 45, which extends over the end of the external gastrostomy tube 55. In one example, the external gastrostomy tube 55 uses a silicone and is French 22 or 24, for example. Various fittings 56, 57 may be provided, such as for inflating the balloon collar 28 through a filling channel 29 or the like, as illustrated in FIG. 7D.

Figure 7F:
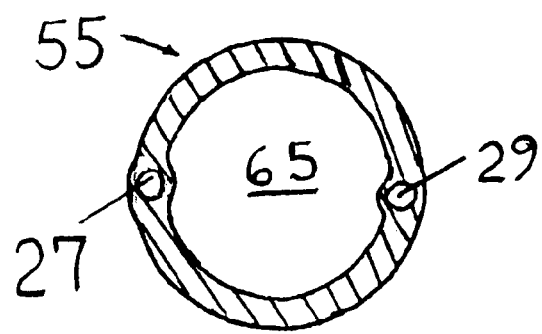

An additional channel 27 may be used for gastric decompression and/or drainage from one of the fittings 56, 57, for example, as illustrated in a radial cross sectional view of the gastrostomy tube 55 of FIG. 7F. In FIG. 7B, an example of a cross section from the end 63 of the external dilator/inserter tube 42 shows a channel 171 and the protective collar/cover 45. FIG. 7C illustrates one example of a protective cover 45 using a plurality of overlapping cover segments 45. In FIG. 7D, a protective collar 45 is illustrated after inflation of the balloon collar 28, which helps to invert the protective collar 45 after insertion of the gastrostomy tube 55 in the stomach 170.

Inflation of the balloon collar 28 retains the gastrostomy tube 55 within the stomach as the internal dilator 42 is removed from the gastrostomy tube 55, for example. The dilator 42, 77 may be curved or straight for proper insertion and placement of the gastrostomy tube 55 within the stomach, and whether curved or straight is withdrawn from the stomach by pulling the dilator 42, 77 through the gastrostomy tube.

In FIG. 7E, a protective collar 45 is made to segment along tear lines 73 to form segmentation of the protective collar 45 upon inflation of the balloon collar 28, allowing easy removal of the dilator and the protective collar 45, for example. The dilator 42, 77 may be removed from the gastrostomy tube 55, when the guide wire 32 is also removed, for example. In one example, this is accomplished without releasing air pressure in the stomach cavity by squeezing or otherwise closing the channels leading through the gastrostomy tube 55. Thus, the gastrostomy tube 55 extends from a location external to the patient through the skin 175, fat 174, musculature 173, and the stomach wall 172, and upon bolstering or other fixation, the tube 55 may be used as a G tube for feeding the patient or delivery of medications through a central channel 65 or an ancillary channel 27, for example.

The protective collar 45 may be made of any material capable of displacement or segmentation when a balloon collar 28 is inflated, for example. In the example of FIG. 7E, the material may be scored or otherwise weakened such that the protective collar 45 splits into leafs at a plurality of tear lines 73. In an alternative example, the protective collar 45 is divided into over-lapping segments, such as illustrated in FIG. 7C, that are likewise withdrawable through the external feeding tube. In yet another example, the protective collar is of a flexible material capable of extending outwardly under the influence of the balloon collar, such that the protective collar 45 inverts, as illustrated in the partial cross sectional view of FIG. 7D.

In one example, a jejunal tube 50 may be inserted through the central channel 65 of the gastrostomy tube 55 allowing both gastric decompression and jejunal feeding, without removal and replacement of the gastrostomy tube 55, resulting in an annular assembly similar to the integrated gastro jejunal tube of FIG. 5. A black silk loop 91 may be disposed at an end of the jejunal tube 50. For example, the black silk loop 91 may have a loop length of about one centimeter, such that the end of the jejunal tube 50 may be sutured, stapled or otherwise fixed in the GI tract, when properly positioned by a surgeon within the jejunum of a patient. An example of such a loop 91 is an Ethicon® K834 black braided silk loop.[4] Silk suture material may be used and may be fashioned in a loop tethered to a terminal end portion of the jejunal tube 50, for example.

[4] Ethicon® is a registered trademark of Johnson and Johnson Corporation, New Brunswick, N.J.

A jejunal tube may use silicone materials or other materials compatible with a gastric environment. In one example, a jejunal tube 50 is a 22-24 French size. Alternatively, the jejunal tube 50 may be 16-18 French size. Balloons may be made of the same materials as the balloon of a Foley catheter, for example, which is known in the art. In one example, one or more of the balloon collars 58, 68, 128, 228 are made of an elastic silicone material capable of extending as a toroid, such as an oblong toroid, as illustrated in 7D, for example. In another example, a polymer film is used that is comparably inflexible that inflates to fill the volume of a balloon collar made of the polymer film but resists further elastic expansion of the toroidal balloon collar of the example.

In one example, a guide wire 32 is used with an external introducer dilator 77 with the guide wire 32 passing through the dilator 77 and the dilator 77 passing through either the gastrostomy tube 55, as illustrated in FIG. 7A, or the jejunal tube 50, as illustrated in FIG. 5, for example. For example, an end of the dilator 77 passes through the jejunal tube 50 such that a protective extension 71 protectively extends as a protective collar over the balloon collar 68 of the jejunal tube 50, protecting the balloon collar 68 during insertion of the jejunal tube 50 through the gastrostomy tube 55 and into the stomach cavity 170. The introducer dilator 77 of the example comprises a central channel 770 through which a guide wire 32 is accommodated, as illustrated in FIG. 6, for example. In FIGS. 5 and 6, an example of a dilator 77 is shown having a collar 71, and a central through hole 770. As illustrated in FIG. 5, the dilator 77 may have a dilator tip 72 and the protective extension 71 may be a protective soft collar that extends over a jejunal balloon collar 68, opposite of the tip 72. While guiding the integrated gastro jejunal tube unit 500 along a guide wire 32, the pointed tip 72 of the introducer dilator 77 may be inserted into the incision and through a hole punched through the stomach wall and into the stomach cavity.

The dilator 77 expands the hole, allowing insertion of the integrated tube unit 500 into the stomach cavity 170. In one example, a portion of the dilator 77 is within the feeding tube, although the dilator end 72 extends from an end of the integrated gastro jejunal tube 500 by a finite distance sufficient to loop the end 72 with the snare 21 from an endoscope 7. For example, the finite distance is about ½ inch or 1.27 cm, The dilator tip 72 may have a flexible collar 71 that extends back up the outer side of the feeding tube by ½ inch, for example. In one example, the dilator tip 72 and its flexible collar 71 form an integrated, seamless unit or a the flexible collar 71 is joined to the dilator tip by molding, heating or bonding. The single unit may be formed from a flexible plastic material, such as a polyurethane, a polyethylene, a polyvinyl, a nylon, a silicone rubber, a co-polymer, a PTFE or the like. By having a portion of the flexible collar 71 extending over the feeding tube's distal end, impingement of the jejunal tube 50 is prevented and the collar 71 prevents the jejunal tube 50 from being held up at the dilation entry point. In addition, this unit prevents a larger dilation entry point into the stomach than necessary to fit the external diameter of the tube and the balloon collar 68. One advantage of using a dilator 77 fit within the jejunal tube 50 is that this prevents larger entry points than required for a feeding tube or other purpose, compared to external dilators known in the art.

In FIG. 6, an example of a cross section from a central portion of the gastric sleeve 55 shows an outer wall of the gastric sleeve 55, a jejunal tube segment 50, and an innermost introducer dilator 77 with a central hole 770. Peripheral channel 51 in the gastric sleeve 55 and peripheral channel 61 in the inner jejunal tube segment 65 may be used respectively to inflate a gastric balloon collar 58 and a jejunal balloon collar 68, respectively.

The gastric sleeve 55 includes a gastric sleeve outlet port 56, for feeding, and gastric drainage holes 52, for draining or feeding, for example. In one example, the gastric sleeve 55 extends from an area including the gastric sleeve outlet port 56 to an area including gastric drainage holes 52 in fluid communication with the outlet port 56. In one example, the gastric sleeve 55, does not communicate at all with the jejunal tube, and is a concentric tube surrounding a portion of the inner jejunal tube segment 65. The drainage holes 52 may be used for gastric decompression, for example.

In FIG. 5, the integrated gastro jejunal tube unit 500 is being pushed in the Y direction, entering the stomach and being advanced under endoscope guidance. A jejunal balloon collar 68 may be distended with normal saline through jejunal balloon port 67. The jejunal balloon collar, in one example, is inflated just before removing the introducer dilator 77, as such inflation will facilitate the inversion of the collar, which comes off the introducer dilator 77 which normally covers the jejunal balloon collar 68 in its deflated state. The introducer dilator 77, which is depicted in FIG. 5 with guide wire 32, is subsequently removed from the external sleeve 50. In one example, guide wire 32 is removed when the jejunal tube is advanced at least 10-12 centimeters into the stomach. An at least partially inflated jejunal balloon collar 68 may help the jejunal tube 50 migrate into the jejunum, as the balloon is pushed by the peristaltic activity of the jejunum.

Figures 8A, 8B:
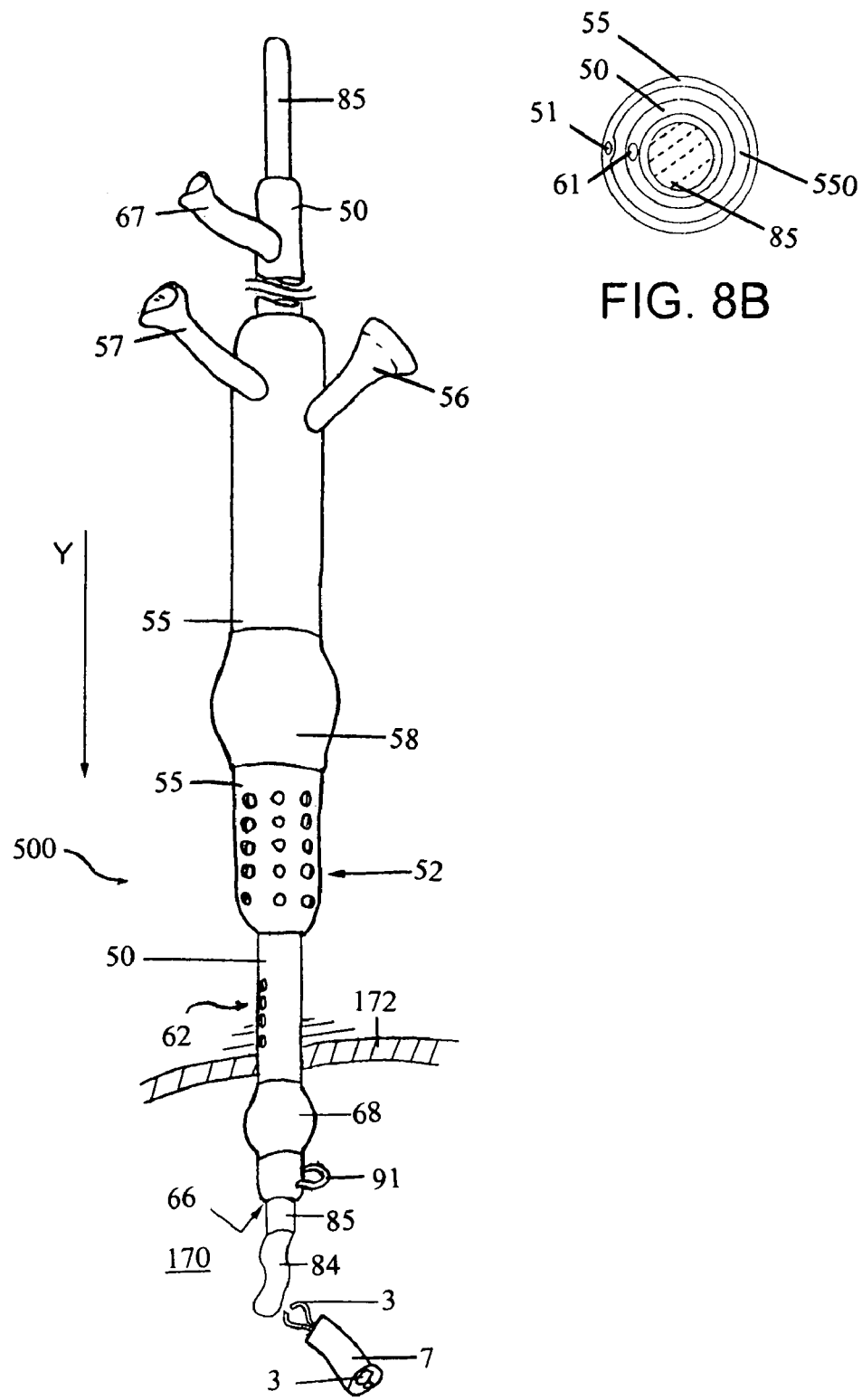
FIG. 8A depicts an example of a step of introducing a guide wire having a stiff portion and a soft tipped portion into the integrated gastro jejunal tube unit.
FIG. 8B illustrates an example of a cross sectional view of a guide wire with a stiff portion and a soft tipped portion.

In FIG. 8A, after removal of the introducer dilator 77 and guide wire 32, a second guide wire 87 having a stiff portion 85 and a soft tip 84, for example, is introduced through the jejunal tube 50 via the jejunal tube outlet port 66. For example, the second guide wire is the Hydra Guidewire® by Boston Scientific.[5]® The snare from the endoscope 7 may be removed and a biopsy forceps 3, such as a Boston Scientific® Radial Jaws® 3 biopsy forceps with a UPN product number of M00515990[6], may be advanced into the stomach through a biopsy channel of the endoscope 7. Alternatively, the endoscope 7 is advanced into the jejunum while dragging the jejunal tube into the jejunum itself, such as by using biopsy forceps to capture the black silk loop or other device disposed at the end of the jejunal tube 50. FIG. 8B illustrates a cross sectional view of the integral gastro jejunal tubes illustrated in FIG. 8A providing an example of a cross section of the stiff portion 85 of the second guide wire, for example.

[5] Hydra Guidewire® is a registered trademark of Boston Scientific Corporation, Natick, Mass.
[6] Boston Scientific® is a registered trademark of Boston Scientific Corporation, Natick, Mass.

Figure 12:
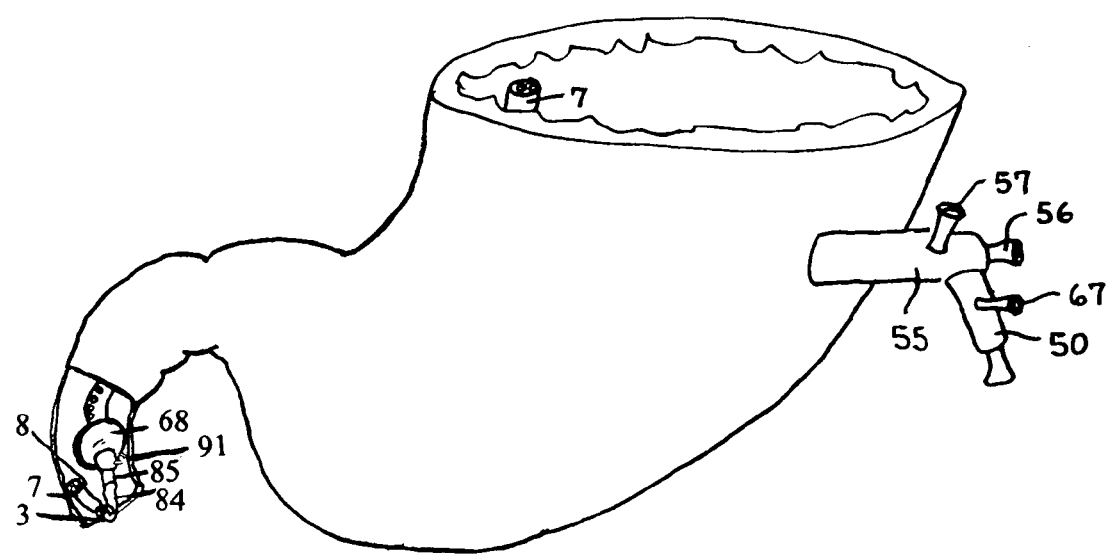
FIG. 12 illustrates another step in a method of introducing the integrated jejunal tube unit.

As shown schematically in FIG. 9, the soft tip 84 of the guide wire 87 is held by the biopsy forceps 3 of the endoscope 7, which may be advanced into the jejunum 300. The gastric sleeve 55 may be guided into the stomach 170 under observation of the endoscope 7, and the gastric balloon collar 58 may be inflated using a saline injected through an inflation port 58, also under observation of the endoscope 7, as illustrated in FIG. 10, for example. The gastric sleeve 55 may be fixed by bolstering, dressing and/or suturing the external tube in place. The integrated gastro jejunal tube unit 500 may be pushed into the stomach 170 simultaneously with advancement of the jejunal tube 50 and the guide wire 84, 85 to help advance the jejunal tube 50 into the jejunum 300. Alternatively, biopsy forceps 3 may be used to drag the guide wire 84, 85 or may be used to capture a black silk loop 91 attached at one end of the jejunal tube 65. Thus, the endoscope 7 may be advanced into the jejunum 300 while dragging the jejunal tube 65 into the jejunum with the endoscope 7, as illustrated in the partial cut away and fenestrated drawings of the examples of FIG. 11 and FIG. 12.

Figure 13:
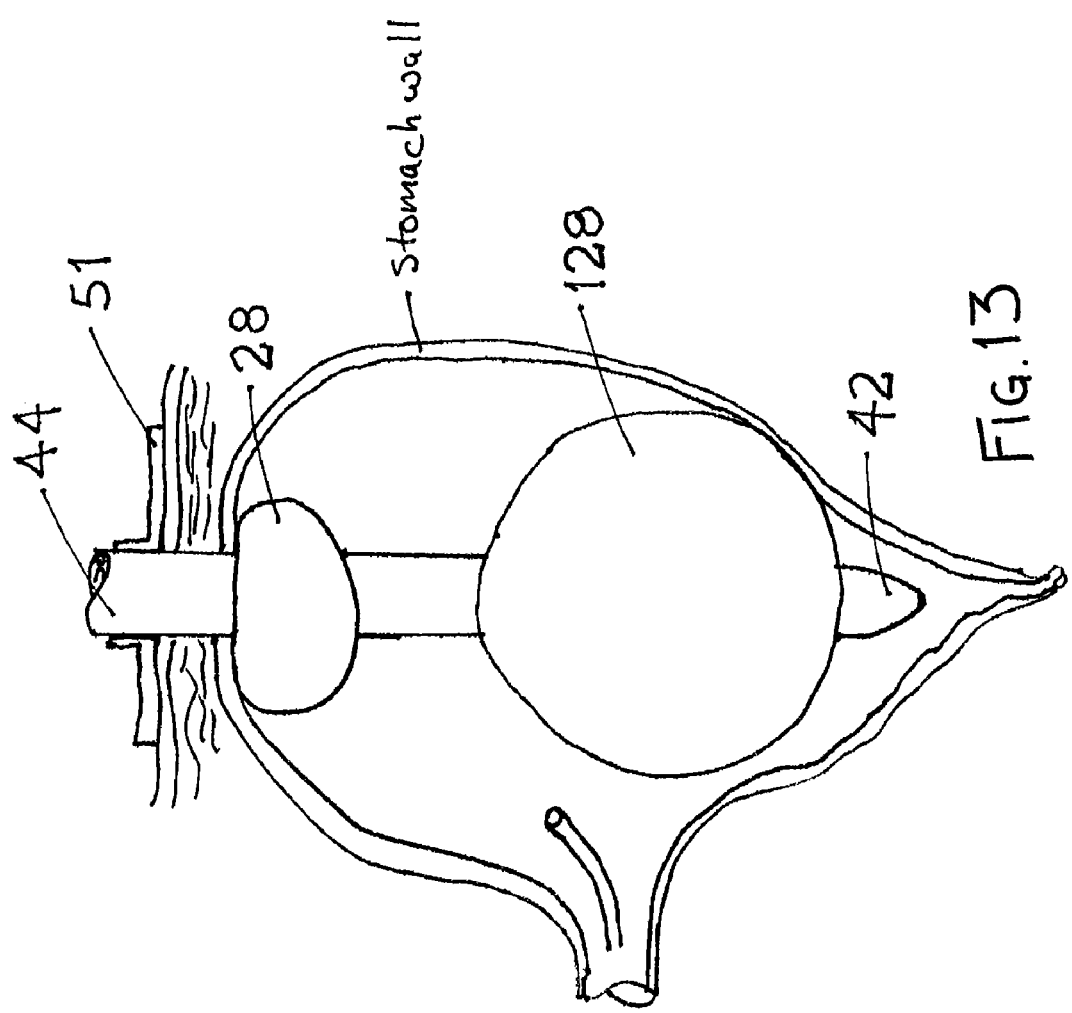
FIG. 13 illustrates an example of a step of introducing an external anchoring device, i.e. bolstering, in a method of introducing an feeding tube and/or weight loss tube.

An external bolster 51 may be used for securing the external tube 44 to the abdominal wall, as shown in the example of FIG. 13, for example. The external bolster 51 may be slid down the exterior wall of the external tube 44. The bolster 51 may be secured in place, such as by friction, a clamp, or sutures, to affix the abdominal musculature and stomach wall between the balloon 28 and the bolster 51, sealing the stoma pierced in the stomach. The area may be suitably dressed. In one example, the external tube 44 is secured to the abdominal wall, under constant view of the endoscope, allowing for precise positioning of a first balloon 28. In the example illustrated in FIG. 13, the external tube 44 includes a second balloon 128 capable of filling a portion of the stomach such that a patient has the sensation of being full. As illustrated in FIG. 13, by adjusting the volume of one or more balloons 28, 128, the patient may be able to lose weight.

Pre and post operative orders may be provided as necessary. In one example, the patient is instructed not to eat or drink for at least 24 hours before and after the feeding tube is inserted, if the patient is conscious. The feeding tube may be attached to a gravity drainage bag through one or more ports in the external tube 44. Antibiotics may be given prophylactically to prevent infection, in one example, either via one of the ports or intravenously.

Use of the Integrated Tube Unit in Eating Disorders, Weight Loss, and Other Treatments In one example, an integrated tube unit is used to assist in weight loss or treatment of eating disorders. In this example, the same procedure is followed. However, the purpose of the integrated tube unit is to expand a balloon inside the stomach to temporarily fill the stomach cavity. In one example, the balloon collar 28 may be inflated using a sterile water, solution or saline, such as 20 milliliter of saline, to seal the stomach wall, while a larger amount of saline may be used for expansion of either the same balloon collar 28 or a second balloon 128 (shown in FIG. 13, for example) having a capacity to fill a substantial portion of the stomach cavity of a patient undergoing treatment for eating disorders or other diseases, at least. In one example, the treatment may temporarily inflate the second balloon in the stomach to give a sensation of fullness during meals. Alternatively, the second balloon 128 may be deflated. Thus, a patient may be trained to eat proper portions or calories may be reduced. FIG. 13 illustrates an external tube 44 having a first port 61 for a first balloon 28 for sealing the stomach and a second port 63 for expanding a separate balloon 128 for filling the stomach cavity, for example. An external feeding tube 44 may have a second channel integrated in the external tube 44, such that the tube 44 may be used either as a feeding tube or a weight control device, for example. Alternatively, a weight control device may omit the central channel 65 and may have a dilator probe affixed to its end After insertion of the jejunal tube 50 fully or part of the way into the jejunum 300 to a sufficient length, the biopsy forceps 3 may be opened, releasing the guide wire 87 or the loop 91, and the biopsy forceps 3 may be removed from endoscope 7. The jejunal tube 50 may be advanced further along the jejunum 300 using the jejunal balloon collar 68, until properly positioned. Then, the jejunal tube 50 may be secured by the loop 91. As illustrated in the fenestrated view of FIG. 14B and the more detailed, schematic view of FIG. 14C, the loop 91 may be sutured, stapled or pinned to the lining of the jejunum 300. For example, a Resolution® clip device, which is a Boston Scientific trademark for a endoscopically deployable clip, may be used to fix the loop 91 to the lining of the jejunum 300, as is known in the art. In one example, such a device has a working length of 235 cm and a working channel of 2.8 mm, and a clip 103 is used to anchor a black silk loop 91 to the wall of the jejunum 300. Anchoring the jejunal tube 50 keeps it in a stationary position after the endoscope 7 is removed. Prior to removal, endoscopic images may be used to visualize the inflation of balloon collars and to check position of the gastric sleeve.

Figure 14A:
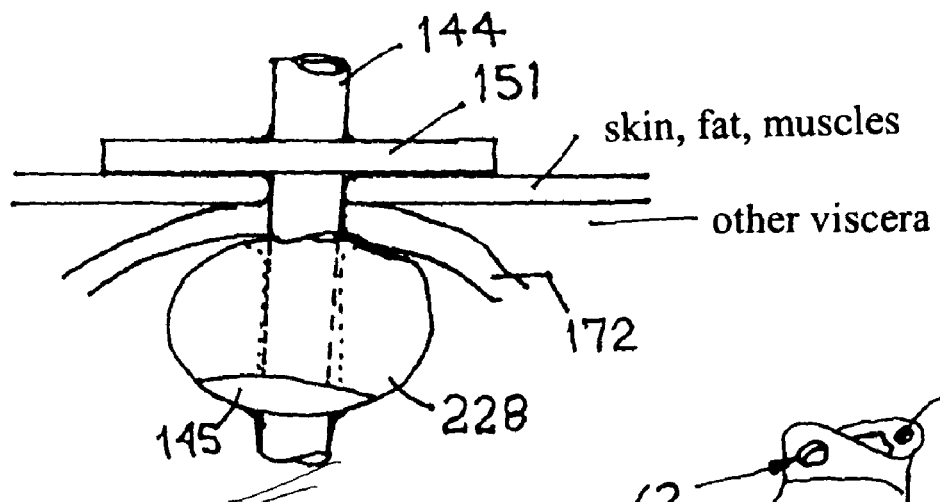
FIG. 14A illustrates a feeding tube with an integrated bolster.
Figure 14C:
FIGS. 14B and 14C illustrate a fenestrated view of the jejunum and a more detailed view of a clip and loop for securing the tip of the jejunal tube.
Figure 14B:
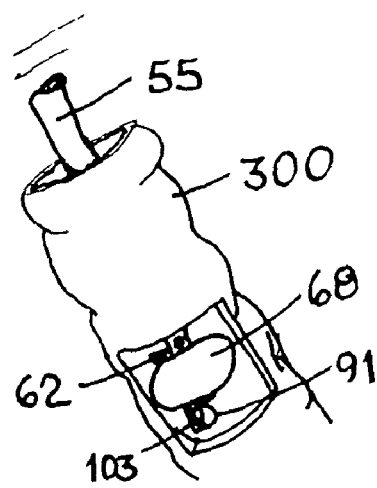

In the example of FIG. 14A a integrated bolster 151 of a gastrostomy tube 144 applies a clamping force between the bolster 151 and a directional collar 145. The external tube 144 includes the directional collar 145, which is of a material that deflects the elastic material of the balloon toward the integrated bolster 151 and clamping the stomach wall 172 and other intervening tissues, 173, 174, 175 between the bolster 151 and the balloon 228. Thus, a separate bolster is not needed.

The gastric balloon collar 58 may be inflated, such as by injecting 20 millileters of saline through port 57, while the balloon 58 is visualized by the endoscope 7. A retention bolster 51, 151 may be affixed externally for securing a gastrostomy tube or the integrated gastro jejunal tube unit 500 in a sealed position, as illustrated schematically in the examples of FIG. 13 and FIG. 14. The inflation of the gastric balloon collar 58, along with the retention bolster, serves to anchor and seal the integrated gastro jejunal unit in the stomach cavity 170 through the abdominal wall, preventing leakage. For example, a retention bolster may be obtained from an EndoVive® kit, which includes a bolster.[7] For example, a 20 French balloon replacement device kit, includes such a bolster and has a UPN number of M00562200. The bolster may be slipped down the shaft of the gastric sleeve for secure affixement using friction, clamp or sutures, for example, Then, the endoscope 7 may be removed and the gastric sleeve outlet port 56 and the jejunal tube outlet port 66 may be connected to gravity drainage bags, for draining of fluids through drainage holes 52, 62.

[7] EndoVive® is a registered trademark of Boston Scientific Corporation, Natick, Mass.

Removal of the Endoscope

A surgeon first makes sure that the gastric sleeve 55 is positioned properly in the stomach. The gastric balloon collar 58 is inflated and bolstered. Then the endoscope 7 is removed from the patient safely after performing one more checks to make sure that no complications have occurred. The patient may be moved to a recovery area, and the following post operative orders may be followed. The patient may be left NPO (nil per os) for 24 hours. The gastric sleeve outlet port 56 and the jejunal tube outlet port 66 may be connected to gravity drainage bags, for drainage of gastric and jejunal contents, and waste. The feeding process, depending on the clinical status, may be initiated using the jejunal tube outlet port 66 or into the gastric sleeve outlet port 56 or both. If gastric emptying is normal, feeding may be initiated via a gastric sleeve outlet port 56. Alternatively, if the GI tract function is abnormal, feeding may be initiated at the jejunal tube outlet port 66.

Removal of the Integrated Gastro Jejunal Tube Unit

In one example, the balloons 58 and 68 are deflated for removal using a syringe. The syringe may be a 20 cc syringe, for example. The integrated gastro jejunal tube unit is then gently pulled from the gastrocutaneous fistula, for example. In one example, an external sleeve which may be of a thin material, is first inserted over the external tube 50 before both the external tube and the sleeve are removed. However, no sleeve is necessary for removal.

If needed, a new integrated gastro jejunal tube unit may be replaced through the gastrocutaneous fistula. The integrated gastro jejunal tube unit, in the post-operative period, may decompress the stomach and simultaneously feed at the jejunal level.

Alternative combinations and variations of the examples provided will become apparent based on this disclosure. It is not possible to provide specific examples for all of the many possible combinations and variations of the embodiments described, but such combinations and variations may be included in claims that eventually issue

What is claimed is:

1. A feeding tube for insertion along a guide wire into a gastrointestinal tract of a patient, comprising:

a gastric tube having a central channel and a feeding inlet at a first end of the gastric tube and a feeding outlet at the opposite end of the central channel;

a balloon expansion inlet at the first end of the gastric tube;

a balloon lumen in fluid communication with the gastric balloon expansion inlet and extending through the gastric tube;

a balloon disposed at the opposite end of the central channel, annularly around the feeding tube, such that the central channel passes through the annular balloon and the balloon is in fluid communication with the balloon lumen and the balloon expansion inlet such that the balloon expands in volume when a volume of fluid is injected into the balloon expansion inlet;

an insertion device extendable through the central channel of the gastric tube and having a protective collar extendable over the balloon such that the balloon is at least temporarily protected from damage during insertion of the feeding tube in the gastrointestinal tract, the insertion device including a hollow shaft into which the guide wire is capable of being fed during insertion of the insertion device, the insertion device and the protective collar providing a transition region for dilating the hole around the guide wire, allowing the gastric tube to be inserted into the patient, and the insertion device being retractable through the central channel of the gastric tube after the feeding tube is inserted into the patient.

2. The feeding tube of claim 1, wherein the balloon is disposed at a distance from the opposite end of the gastric tube, and the gastric tube includes holes extending through the thickness of a portion of the gastric tube disposed between the gastric balloon and an opposite end of the gastric tube disposed opposite of the first end of the gastric tube.

3. The feeding tube of claim 1, further comprising a jejunal tube, the jejunal tube extending through the central channel of the gastric tube and having a jejunal channel extending the central channel from the feeding inlet to the feeding outlet at a distal end of the jejunal tube extending from the gastric tube such that the insertion device is extendable through the jejunal channel and the central channel of the gastric tube for insertion of the jejunal tube and the gastric tube in the gastrointestinal tract.

4. The feeding tube of claim 3, wherein the balloon is a jejunal balloon and the balloon expansion inlet is a jejunal balloon expansion inlet at the first end of the gastric tube and the lumen is a jejunal balloon lumen in fluid communication with the jejunal balloon expansion inlet.

5. The feeding tube of claim 4, wherein the protective collar extends over the jejunal balloon such that the jejunal balloon is at least temporarily protected from damage during insertion of the feeding tube into the gastrointestinal tract, and the feeding tube further comprising a gastric balloon annularly disposed proximal to an end of the gastric tube.

6. The feeding tube of claim 5, wherein expansion of the jejunal balloon permits the insertion device and the protective collar of the insertion device to be removed from the jejunal tube.

7. The feeding tube of claim 6, wherein expansion of the jejunal balloon results in segmentation of the protective collar.

8. The feeding tube of claim 6, wherein the protective collar is comprised of overlapping segments, and the overlapping segments are not attached along at least a portion of a length of the overlapping segments.

9. The feeding tube of claim 4, wherein jejunal balloon is capable of expanding to block off a portion of the jejunum, when the jejunal balloon is expanded by injecting a first volume of fluid into the jejunal balloon.

10. The feeding tube of claim 4, wherein the jejunal balloon is capable of blocking the feeding outlet, when the jejunal balloon is expanded by injecting a second volume of fluid into the jejunal balloon.

11. The feeding tube of claim 4, wherein the jejunal tube has a loop extending from a tip of the jejunal tube.

12. The feeding tube of claim 4, wherein a clip is used to secure the loop and the tip of the jejunal tube within the gastrointestinal tract.

13. The feeding tube of claim 4, wherein the gastric tube and the jejunal tube form an annular cavity or at least one channel disposed between the gastric tube and the jejunal tube.

14. The feeding tube of claim 13, wherein the gastric tube and the jejunal tube form an annular cavity disposed between the wall of the gastric tube and the wall of the jejunal tube, such that holes extending through a thickness of the gastric tube at a second end of the gastric tube, opposite of the first end of the gastric tube, are in fluid communication with an drainage outlet disposed proximally to the first end of the gastric tube.

15. The feeding tube of claim 1, wherein the protective collar is extendable over the gastric balloon.

16. The feeding tube of claim 1, further comprising a second balloon in addition to the balloon recited in claim 1, wherein the second balloon and the balloon recited in claim 1 are both disposed proximal the feeding outlet at the opposite end of the central channel.

17. The feeding tube of claim 16, wherein the volume of the balloon recited in claim 1 or the volume of the second balloon is greater than twenty millimeters.

18. The feeding tube of claim 17, wherein the volume of the balloon recited in claim 1 is much greater than the volume of the second balloon, when fully inflated, and the second balloon is disposed between the feeding inlet and the balloon recited in claim 1.

19. The feeding tube of claim 1, wherein the gastric tube includes an integrated bolster fixed on the gastric tube and extending outwardly from a circumference of the gastric tube.

20. The feeding tube of claim 19, wherein the gastric tube includes a balloon collar disposed relative to the gastric balloon such that the gastric balloon is deflected by the balloon collar in the direction of integrated bolster whereby the gastric balloon and the integrated bolster develop a clamping force between the gastric balloon and the integrated bolster.

* * * * *